(12) United States Patent
Jeon et al.

(10) Patent No.: US 11,505,467 B2
(45) Date of Patent: Nov. 22, 2022

(54) HIGH FUNCTIONALIZATION DENSITY GRAPHENE

(71) Applicant: Massachusetts Institute of Technology, Cambridge, MA (US)

(72) Inventors: Intak Jeon, Boston, MA (US); Timothy M. Swager, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 204 days.

(21) Appl. No.: 16/182,371

(22) Filed: Nov. 6, 2018

(65) Prior Publication Data

US 2019/0135637 A1    May 9, 2019

Related U.S. Application Data

(60) Provisional application No. 62/582,074, filed on Nov. 6, 2017.

(51) Int. Cl.
 *C01B 32/225* (2017.01)
 *C01B 32/21* (2017.01)
 (Continued)

(52) U.S. Cl.
 CPC .......... *C01B 32/225* (2017.08); *C01B 32/194* (2017.08); *C01B 32/21* (2017.08);
 (Continued)

(58) Field of Classification Search
 None
 See application file for complete search history.

(56) References Cited

U.S. PATENT DOCUMENTS

| | | |
|---|---|---|
| 3,450,878 A | 6/1969 | Pezdirtz et al. |
| 3,915,706 A | 10/1975 | Limburg et al. |

(Continued)

FOREIGN PATENT DOCUMENTS

| | | |
|---|---|---|
| CN | 1995143 A | 7/2007 |
| JP | 63-221278 A | 9/1988 |

(Continued)

OTHER PUBLICATIONS

Shi et al.; High-yield Production of Highly Conductive Graphene via Reversible Covalent Chemistry; Chem. Commun., 51, 2806-2809; 2015.*

(Continued)

*Primary Examiner* — Guinever S Gregorio
(74) *Attorney, Agent, or Firm* — Wolf, Greenfield & Sacks, P.C.

(57) ABSTRACT

Carbon-based materials, and associated methods and articles, are generally provided. In some embodiments, a carbon-based material comprises a carbon-based portion and a functional group bonded to the carbon-based portion. The functional group may be capable of forming a reversible covalent bond with a species. Carbon may make up greater than or equal to 30 wt % of the carbon-based portion. The carbon-based portion may comprise graphene, and a ratio of a total number of functional groups in a plurality of functional groups bonded to the graphene to a total number of carbon atoms in the plurality of carbon atoms of the graphene may be greater than or equal to 1:50. The carbon-based portion may comprise graphene, and greater than or equal to 70% of the graphene sheets may be spaced apart from their nearest neighbors by a distance of greater than or equal to 10 Å. A method may comprise applying a voltage to a carbon-based material. The voltage may be applied in the presence of a combination of solvents comprising a (Continued)

dissolved species. The combination of solvents may comprise a solvent stable at voltages of greater than or equal to −3.15 V and less than or equal to −2.2 V and/or may comprise a solvent with a surface tension within 25% of a surface tension of the carbon-based material. The voltage may be a decreasing voltage that decreases at a rate of greater than or equal to 2 µV/s and less than or equal to 40 µV/s and has a value of greater than or equal to −2.2 V and less than or equal to −3.15 V at at least one point in time.

22 Claims, 19 Drawing Sheets

(51) Int. Cl.

| | | |
|---|---|---|
| C01B 32/194 | (2017.01) | |
| G01N 27/327 | (2006.01) | |
| G01N 33/53 | (2006.01) | |
| B82Y 40/00 | (2011.01) | |
| B82Y 30/00 | (2011.01) | |

(52) U.S. Cl.
CPC ..... *G01N 27/3271* (2013.01); *G01N 33/5306* (2013.01); *B82Y 30/00* (2013.01); *B82Y 40/00* (2013.01)

(56) References Cited

U.S. PATENT DOCUMENTS

| | | | |
|---|---|---|---|
| 4,616,237 A | 10/1986 | Pettigrew et al. | |
| 5,753,088 A | 5/1998 | Olk | |
| 6,616,497 B1 | 9/2003 | Choi et al. | |
| 6,652,958 B2 | 11/2003 | Tobita | |
| 6,705,910 B2 | 3/2004 | Sheu et al. | |
| 6,902,658 B2 | 6/2005 | Talin et al. | |
| 6,958,216 B2 | 10/2005 | Kelley et al. | |
| 7,014,743 B2 | 3/2006 | Zhou et al. | |
| 7,187,115 B2 | 3/2007 | Seon | |
| 7,303,875 B1 | 12/2007 | Bock et al. | |
| 7,365,100 B2 | 4/2008 | Kuper et al. | |
| 7,556,775 B2 | 7/2009 | McGill et al. | |
| 7,854,826 B2 | 12/2010 | So et al. | |
| 7,871,533 B1 | 1/2011 | Haiping et al. | |
| 8,187,887 B2 | 5/2012 | Swager et al. | |
| 8,212,132 B2 | 7/2012 | Swager et al. | |
| 8,426,208 B2 | 4/2013 | Swager et al. | |
| 8,456,073 B2 | 6/2013 | Swager et al. | |
| 8,476,510 B2 | 7/2013 | Swager et al. | |
| 8,735,313 B2 | 5/2014 | Swager et al. | |
| 8,951,473 B2 | 2/2015 | Wang et al. | |
| 9,114,377 B2 | 8/2015 | Swager et al. | |
| 9,267,908 B2 | 2/2016 | Wang et al. | |
| 9,770,709 B2 | 9/2017 | Swager et al. | |
| 11,091,369 B2 * | 8/2021 | Hunter ................ | C10M 103/02 |
| 2002/0037457 A1 | 3/2002 | Choi | |
| 2002/0171079 A1 | 11/2002 | Braun et al. | |
| 2004/0067530 A1 | 4/2004 | Gruner | |
| 2004/0161360 A1 | 8/2004 | Ogawa et al. | |
| 2005/0067406 A1 | 3/2005 | Rajarajan et al. | |
| 2005/0070658 A1 | 3/2005 | Ghosh et al. | |
| 2006/0045838 A1 | 3/2006 | Lucien Malenfant et al. | |
| 2006/0057927 A1 | 3/2006 | Kang et al. | |
| 2006/0063464 A1 | 3/2006 | Kang et al. | |
| 2006/0142148 A1 | 6/2006 | Ma et al. | |
| 2006/0151382 A1 | 7/2006 | Petrik | |
| 2006/0174385 A1 | 8/2006 | Gruber et al. | |
| 2006/0202168 A1 | 9/2006 | Barrera et al. | |
| 2007/0178477 A1 | 8/2007 | Joiner et al. | |
| 2007/0179272 A1 | 8/2007 | Tobe et al. | |
| 2007/0295347 A1 | 12/2007 | Paine et al. | |
| 2008/0076816 A1 | 3/2008 | Bianco et al. | |
| 2008/0131658 A1 | 6/2008 | Wakharkar et al. | |
| 2008/0221240 A1 | 9/2008 | Swager et al. | |
| 2008/0302998 A1 | 12/2008 | Hong et al. | |
| 2009/0058258 A1 | 3/2009 | Chang et al. | |
| 2009/0305089 A1 | 12/2009 | Minteer et al. | |
| 2009/0306427 A1 | 12/2009 | Martinez-Rubi | |
| 2010/0028559 A1 | 2/2010 | Yan et al. | |
| 2010/0159366 A1 | 6/2010 | Shao-Horn et al. | |
| 2010/0179054 A1 | 7/2010 | Swager et al. | |
| 2010/0222432 A1 | 9/2010 | Hua | |
| 2011/0089051 A1 | 4/2011 | Wang et al. | |
| 2011/0136007 A1 | 6/2011 | Zhamu et al. | |
| 2011/0171629 A1 | 7/2011 | Swager et al. | |
| 2012/0116094 A1 | 5/2012 | Swager et al. | |
| 2012/0171093 A1 | 7/2012 | Swager et al. | |
| 2012/0295360 A1 | 11/2012 | Swager et al. | |
| 2013/0113359 A1 | 5/2013 | Swager et al. | |
| 2013/0123514 A1 * | 5/2013 | Bielawski ................ | B01J 8/067 |
| | | | 549/72 |
| 2014/0107326 A1 | 4/2014 | Swager et al. | |
| 2015/0336092 A1 | 11/2015 | Swager et al. | |
| 2018/0298154 A1 * | 10/2018 | Lundorf ................ | C09D 11/03 |

FOREIGN PATENT DOCUMENTS

| | | |
|---|---|---|
| JP | 2006-509703 A | 3/2006 |
| JP | 2007-524735 A | 8/2007 |
| JP | 2008-047855 A | 2/2008 |
| JP | 2008-520414 A | 6/2008 |
| JP | 2009-022919 A | 2/2009 |
| JP | 2009-268961 A | 11/2009 |
| JP | 2010-129385 A | 6/2010 |
| WO | WO 01/10779 A1 | 2/2001 |
| WO | WO 2004/052783 A2 | 6/2004 |
| WO | WO 2004/113275 A2 | 12/2004 |
| WO | WO 2006/055670 A2 | 5/2006 |
| WO | WO 2006/104046 A1 | 10/2006 |
| WO | WO 2006/115486 A1 | 11/2006 |
| WO | WO 2007/033189 A1 | 3/2007 |
| WO | WO 2007/098578 A1 | 9/2007 |
| WO | WO 2007/143028 A2 | 12/2007 |
| WO | WO 2008/026304 A1 | 3/2008 |
| WO | WO 2008/133779 A2 | 11/2008 |
| WO | WO 2009/085015 A1 | 7/2009 |
| WO | WO 2009/136978 A2 | 11/2009 |
| WO | WO 2010/022164 A1 | 2/2010 |
| WO | WO 2012/061607 A2 | 5/2012 |

OTHER PUBLICATIONS

International Search Report and Written Opinion for PCT/US2008/003180 dated Jun. 19, 2009.
International Preliminary Report on Patentability for PCT/US2008/003180 dated Sep. 17, 2009.
Invitation to Pay Additional Fees for PCT/US2009/001396 dated Dec. 10, 2009.
International Search Report and Written Opinion for PCT/US2009/001396 dated Apr. 22, 2010.
International Preliminary Report on Patentability for PCT/US2009/001396 dated Sep. 16, 2010.
International Search Report and Written Opinion for PCT/US2009/006512 dated Oct. 22, 2010.
International Preliminary Report on Patentability for PCT/US2009/006512 dated Jun. 23, 2011.
Invitation to Pay Additional Fees for PCT/US2010/051610 dated Dec. 27, 2011.
International Search Report and Written Opinion for PCT/US2010/051610 dated Mar. 5, 2012.
International Preliminary Report on Patentability for PCT/US2010/051610 dated Apr. 19, 2012.
Invitation to Pay Additional Fees for PCT/US2010/055395 dated Dec. 7, 2011.
International Search Report and Written Opinion for PCT/US2010/055395 dated Mar. 20, 2012.
International Preliminary Report on Patentability for PCT/US2010/055395 dated May 18, 2012.
International Search Report and Written Opinion for PCT/US2011/059155 dated Jun. 25, 2013.

(56) References Cited

OTHER PUBLICATIONS

International Preliminary Report on Patentability for PCT/US2011/059155 dated Jul. 11, 2013.
International Search Report and Written Opinion for PCT/US2011/059168 dated Jun. 19, 2013.
International Preliminary Report on Patentability for PCT/US2011/059168 dated Jul. 18, 2013.
International Search Report and Written Opinion for Application No. PCT/US2013/029621 dated May 8, 2013.
International Preliminary Report on Patentability for PCT/US2013/029621 dated Apr. 30, 2015.
[No Author Listed] TGP- H Carbon Fiber Paper. Toray Automotive Solutions. Toray Industries (America), Inc. Available at http://www.toray-auto.us/poductrs/carbon_papers_fuel_cells.html. Last accessed Nov. 19, 2010. 2 pages.
[No Author] Definition of "ketone," accessed online at http://dictionary.reference.com/browse/ketone?s=t on Jun. 14, 2014. 2 pages.
[No Author] Definition of "moiety," accessed online at http://dictionary.reference.com/browse/moiety on Dec. 21, 2014. 3 pages.
Albert et al., Cross-reactive chemical sensor arrays. Chem Rev. Jul. 12, 2000;100(7):2595-626.
Araujo et al., Phonon self-energy corrections to nonzero wavevector phonon modes in single-layer graphene. Phys Rev Lett. Jul. 27, 2012;109(4):046801(1-5). Epub Jul. 24, 2012.
Artamkina et al., Some aspects of anionic .sigma.-complexes. Chem Rev. 1982;82(4):427-59.
Bai et al., Gas Sensors Based on Conducting Polymers. Sensors. 2007;7:267-307.
Balandin, Thermal properties of graphene and nanostructured carbon materials. Nat Mater. Aug. 2011;10(8):569-81. doi: 10.1038/nmat3064. Epub Jul. 22, 2011.
Barton et al., Electroreduction of $O_2$ to Water on the "Wired" Laccase Cathode. J Phys Chem B. 2001;105(47):11917-21. Epub Oct. 12, 2001.
Baughman et al., Carbon Nanotubes—The Route Toward Applications. Science. 2002;297(2):787-92.
Becker et al., The Influence of Surface Strain on the Chemical Reactivity of Fullerene Ions: Addition Reactions with Cyclopentadiene and 1,3-cycolhexadiene. International Journal of Mass Spectrometry and Ion Processes. 1997;167/168:519-24.
Belanger et al., Electrografting: a powerful method for surface modification. Chem Soc Rev. Jul. 2011;40(7):3995-4048. doi: 10.1039/c0cs00149j. Epub Apr. 18, 2011.
Brownson et al., Graphene electrochemistry: fundamental concepts through to prominent applications. Chem Soc Rev. Nov. 7, 2012;41(21):6944-76. doi: 10.1039/c2cs35105f. Epub Aug. 1, 2012.
Chacon-Torres et al., Raman spectroscopy of graphite intercalation compounds: Charge transfer, strain, and electron-phonon coupling in graphene layers. Phys Status Solidi B. Dec. 2014;251(12):2337-55. Epub Nov. 21, 2014.
Chen et al., Dissolution of Full-Length Single-Walled Carbon Nanotubes. J Phys Chem B. 2001;105:2525-28.
Chen et al., Noncovalent functionalization of carbon nanotubes for highly specific electronic biosensors. Proc Natl Acad Sci U S A. Apr. 29, 2003;100(9):4984-9. Epub Apr. 15, 2003.
Chua et al., Chemical reduction of graphene oxide: a synthetic chemistry viewpoint. Chem Soc Rev. Jan. 7, 2014;43(1):291-312. doi: 10.1039/c3cs60303b. Epub Oct. 11, 2013.
Coffey et al., Conducting Polymer/Graphite Fiber Composites for High Charge Density Battery Electrodes. Lithium batteries—Symposium. Proceedings—Electrochemical Society. New Orleans, LA. Oct. 1993. The Society. 1994;94-4:258-68.
Coffey et al., High charge density conducting polymer/graphite fiber composite electrodes for battery applications. J Electrochem Soc. 1995;142(2):321-25.
Collins et al., Extreme oxygen sensitivity of electronic properties of carbon nanotubes. Science. Mar. 10, 2000;287(5459):1801-4.

Collins et al., Graphene oxide as an electrophile for carbon nucleophiles. Chem Commun (Camb). Aug. 21, 2011;47(31):8790-2. Epub Jul. 7, 2011.
Das et al., Monitoring dopants by Raman scattering in an electrochemically top-gated graphene transistor. Nat Nanotechnol. Apr. 2008;3(4):210-5. doi: 10.1038/nnano.2008.67. Epub Mar. 30, 2008.
Dato et al., Substrate-free gas-phase synthesis of graphene sheets. Nano Lett. Jul. 2008;8(7):2012-6. doi: 10.1021/nl8011566. Epub Jun. 5, 2008.
Diederich et al., Covalent Fullerene Chemistry. Science. 1996;271:317-23.
Dimtev et al., Direct real-time monitoring of stage transitions in graphite intercalation compounds. ACS Nano. Mar. 26, 2013;7(3):2773-80. doi: 10.1021/nn400207e. Epub Feb. 26, 2013.
Doll et al., Raman scattering study of the high-frequency graphitic intralayer modes in Li-graphite and the stage dependence of the mode frequency in donor graphite intercalation compounds. Phys Rev B Condens Matter. Sep. 15, 1987;36(9):4940-4945.
Dresselhaus et al., Intercalation compounds of graphite. Adv Phys. 1981;30(2):139-326.
Dreyer et al., The chemistry of graphene oxide. Chem Soc Rev. Jan. 2010;39(1):228-40. doi: 10.1039/b917103g. Epub Nov. 3, 2009.
Duong et al., Probing graphene grain boundaries with optical microscopy. Nature. Oct. 11, 2012;490(7419):235-9. Suppl 1 pg. doi: 10.1038/nature11562. Epub Oct. 3, 2012.
Dwyer et al., DNA-functionalized single-walled carbon nanotubes. Nanotechnology. 2002;13(5):601-04.
Eckmann et al., Probing the nature of defects in graphene by Raman spectroscopy. Nano Lett. Aug. 8, 2012;12(8):3925-30. doi: 10.1021/nl300901a. Epub Jul. 5, 2012.
Eda et al., Blue photoluminescence from chemically derived graphene oxide. Adv Mater. Jan. 26, 2010;22(4):505-9. doi: 10.1002/adma.200901996.
Englert et al., Covalent bulk functionalization of graphene. Nature Chemistry. Apr. 2011;3:279-86.
Ferrari, Raman spectroscopy of graphene and graphite: Disorder, electron-phonon coupling, doping and nonadiabatic effects. Solid State Commun. Jul. 2007;143(1-2):47-57.
Frank et al., Compression behavior of single-layer graphenes. ACS Nano. Jun. 22, 2010;4(6):3131-8. doi: 10.1021/nn100454w. Epub May 24, 2010.
Frank et al., Raman 2D-band splitting in graphene: theory and experiment. ACS Nano. Mar. 22, 2011;5(3):2231-9. doi: 10.1021/nn103493g. Epub Feb. 14, 2011.
Fry et al., Electrolyte effects upon the polarographic reduction of alkyl halides in dimethyl sulfoxide. J Org Chem. Jan. 1976;41(1):54-7.
Geim et al., The rise of graphene. Nat Mater. Mar. 2007;6(3):183-91.
Georgakilas et al., Functionalization of graphene: covalent and non-covalent approaches, derivatives and applications. Chem Rev. Nov. 14, 2012;112(11):6156-214. doi: 10.1021/cr3000412. Epub Sep. 25, 2012.
Georgakilas et al., Organic functionalization of carbon nanotubes. J Am Chem Soc. Feb. 6, 2002;124(5):760-1.
Giordani et al., Multifunctional hybrid materials composed of [60]fullerene-based functionalized-single-walled carbon nanotubes. Carbon. 2009;47(3):578-88.
Guo et al., Covalently bridging gaps in single-walled carbon nanotubes with conducting molecules. Science. Jan. 20, 2006;311(5759):356-9.
Hahm et al., Direct Ultrasensitive Electrical Detection of DNA and DNA Sequence Variations Using Nanowire Nanosensors. Nano Letters. 2004; 4(1):51-54.
Hanson et al., Sandmeyer reactions. Part 7. An investigation into the reduction steps of Sandmeyer hydroxylation and chlorination reactions. J Chem Soc., Perkin Trans. 2. May 2002;2(6):1135-50. Epub Apr. 19, 2002.
Haubner et al., The route to functional graphene oxide. Chemphyschem. Jul. 12, 2010;11(10):2131-9.
Janata et al., Conducting polymers in electronic chemical sensors. Nat Mater. Jan. 2003;2(1):19-24.

(56) References Cited

OTHER PUBLICATIONS

Jung et al., Covalent attachment and hybridization of DNA oligonucleotides on patterned single-walled carbon nanotube films. Langmuir. Sep. 28, 2004;20(20):8886-91.

Kamat et al., Self-Assembled Linear Bundles of Single Wall Carbon Nanotubes and Their Alignment and Deposition as a Film in a dc Field. J Am Chem Soc. 2004;126(34):10757-62.

Khare et al., Carbon Nanotube Based Composites—A Review. Journal of Minerals & Materials Characterization & Engineering. 2005; 4(1):31-46.

Kolmakov et al., Chemical Sensing and Catalysis by One-Dimensional Metal-Oxide Nanostructures. Annu Rev Mater Res. 2004;34:151-80.

Kong et al., Nanotube molecular wires as chemical sensors. Science. Jan. 28, 2000;287(5453):622-5.

Kovtyukhova et al., Non-oxidative intercalation and exfoliation of graphite by Brønsted acids. Nat Chem. Nov. 2014;6(11):957-63. doi: 10.1038/nchem.2054. Epub Sep. 7, 2014.

Kubat et al., Degradation of pyrene by UV radiation. Journal of Photochemistry and Photobiology A: Chemistry. 2000;132:33-36.

Lee et al., Estimation of Young's modulus of graphene by Raman spectroscopy. Nano Lett. Sep. 12, 2012;12(9):4444-8. doi: 10.1021/n1301073q. Epub Aug. 6, 2012.

Lee et al., Measurement of the elastic properties and intrinsic strength of monolayer graphene. Science. Jul. 18, 2008;321(5887):385-8. doi: 10.1126/science.1157996.

Li et al., Processable aqueous dispersions of graphene nanosheets. Nat Nanotechnol. Feb. 2008;3(2):101-5. doi: 10.1038/nnano.2007.451. Epub Jan. 27, 2008.

Liang et al., $Co_3O_4$ nanocrystals on graphene as a synergistic catalyst for oxygen reduction reaction. Nat Mater. Oct. 2011;10(10):780-6.

Liu et al., Fullerene pipes. Science. May 22, 1998;280(5367):1253-6.

Liu et al., The dependence of graphene Raman D-band on carrier density. Nano Lett. 2013;13(12):6170-5. doi: 10.1021/n14035048. Epub Nov. 27, 2013.

Lobez et al., Radiation Detection: Resistivity Responses in Functional Poly (Olefin Sulfone)/Carbon Nanotube Composites. Angew Chem Int Ed. 2010; 49:95-98.

Loh et al., The chemistry of graphene. Journal of Materials Chemistry. Mar. 28, 2010;20(12):2277-89.

Lotya et al., Liquid phase production of graphene by exfoliation of graphite in surfactant/water solutions. J Am Chem Soc. Mar. 18, 2009;131(10):3611-20. doi: 10.1021/ja807449u. Epub Feb. 19, 2009.

Lutz, 1,3-Dipolar cycloadditions of azides and alkynes: a universal ligation tool in polymer and materials science. Angew Chem Int Ed. 2007; 46:1018-25.

Ma et al., Interfacial properties and impact toughness of dendritic hexamethylenetetramine functionalized carbon fiber with varying chain lengths. RSC Adv. 2014;4:39156-66.

Maggini et al., Addition of Azomethine Ylides to C60: Synthesis, Characterization, and Functionalization of Fullerene Pyrrolidines. J Am Chem Soc. 1993;115:9798-99.

Mahadevi et al., Cation-π interaction: its role and relevance in chemistry, biology, and material science. Chem Rev. Mar. 13, 2013;113(3):2100-38. doi: 10.1021/cr300222d. Epub Nov. 13, 2012.

McQuade et al., Conjugated Polymer-Based Chemical Sensors. Chem Rev. 2000;100:2537-74.

Moses et al., The growing applications of click chemistry. Chem Soc Rev. Aug. 2007;36(8):1249-62. Epub May 3, 2007.

Nemanich et al., Raman scattering from intercalated donor compounds of graphite. Phys Rev B. Sep. 15, 1977;16(6):2965-72.

Ni et al., Graphene thickness determination using reflection and contrast spectroscopy. Nano Lett. Sep. 2007;7(9):2758-63. Epub Jul. 26, 2007.

Novoselov et al., A roadmap for graphene. Nature. Oct. 11, 2012;490(7419):192-200. doi: 10.1038/nature11458.

O'Donovan et al., Phosphine-catalysed cycloaddition of buta-2,3-dienoates and but-2-ynoates to [60]fullerene. Chem Commun. 1997:81-82.

Park et al., Enhancement of the field-effect mobility of poly(3-hexylthiophene)/functionalized carbon nanotube hybrid transistors. Org Electron. 2008;9:317-22.

Parvez et al., Electrochemically exfoliated graphene as solution-processable, highly conductive electrodes for organic electronics. ACS Nano. Apr. 23, 2013;7(4):3598-606. doi: 10.1021/nn400576v. Epub Mar. 26, 2013.

Parvez et al., Exfoliation of graphite into graphene in aqueous solutions of inorganic salts. J Am Chem Soc. Apr. 23, 2014;136(16):6083-91. doi: 10.1021/ja5017156. Epub Mar. 31, 2014.

Paul et al., Sequestration and selective oxidation of carbon monoxide on graphene edges. Journal of Physics: Condensed Matter. Sep. 2, 2009;21(35):355008(1-8).

Paulus et al., Covalent electron transfer chemistry of graphene with diazonium salts. Acc Chem Res. Jan. 15, 2013;46(1):160-70. doi: 10.1021/ar300119z. Epub Sep. 4, 2012.

Pederson et al., Core particle, fiber, and transcriptionally active chromatin structure. Annu Rev Cell Biol. 1986;2:117-47.

Potyrailo, Polymeric Sensoir Materials: Toward an Alliance of Combinatorial and Rational Design Tools? Agnew Chem Int Ed. 2006;45:702-23.

Prato et al., Fulleropyrrolidines: A Family of Full-Fledged Fullerene Derivatives. Acc Chem Res. 1998;31(9):519-26.

Preda et al., Addition of Dihalocarbenes to Corannulene. A Fullerene-Type Reaction. Tetrahedron Letters. 2000;41:9633-37.

Qi et al., Toward Large Arrays of Multiplex Functionalized Carbon Nanotube Sensors for Highly Sensitive and Selective Molecular Detection. Nano Lett. 2003;3(3):347-51.

Ramanathan et al., Functionalized graphene sheets for polymer nanocomposites. Nat Nanotechnol. Jun. 2008;3(6):327-31. Epub May 11, 2008.

Raval et al., Determining ionizing radiation using sensors based on organic semiconducting material. Appl Phys Lett. 2009;94:123304-1-123304-3.

Richard et al., New insight into 4-nitrobenzene diazonium reduction process: Evidence for a grafting step distinct from $NO_2$ electrochemical reactivity. J Electroanal Chem. Oct. 1, 2012;685:109-15. Epub Sep. 24, 2012.

Robertson et al., Electronic and atomic structure of amorphous carbon. Phys Rev B Condens Matter. Feb. 15, 1987;35(6):2946-2957.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Santhanam et al., A chemical sensor for chloromethanes using a nanocomposite of multiwalled carbon nanotubes with poly(3-methylthiophene). Sensors and Actuators B. 2005;106:766-71.

Scott, Fragments of Fullerenes: Novel Syntheses, Structures and Reactions. Pure & Appl Chem., 1996;68(2):291-300.

Serp et al., Carbon Nanotubes and Nanofibers in Catalysis. Applied Catalysis A: General. 2003;253:337-58.

Shih et al., Bi- and trilayer graphene solutions. Nature Nanotechnology. Jul. 2011;6:439-45.

Shu et al., Electrochemical Intercalation of Lithium into Graphite. J. Electrochem. Soc. Apr. 1993;140(4): 922-927.

Shu et al., Phosphine-catalysed [3 + 2] cycloadditions of buta-2,3-dienoates with [60]fullerene. Chem Commun. 1997;79-80.

Silverman, The Organic Chemistry of Drug Design and Drug Action. 2nd ed. 2004;29-32.

Sirisaksoontorn et al., Preparation and characterization of a tetrabutylammonium graphite intercalation compound. J Am Chem Soc. Aug. 17, 2011;133(32):12436-8. doi: 10.1021/ja2053539. Epub Jul. 22, 2011.

Snow et al., Chemical detection with a single-walled carbon nanotube capacitor. Science. Mar. 25, 2005;307(5717):1942-5.

Star et al., Electronic Detection of Specific Protein Binding Using Nanotube FET Devices. Nano Lett. 2003;3(4):459-63. Supporting Information inlcluded.

(56) References Cited

OTHER PUBLICATIONS

Star et al., Nanoelectronic Carbon Dioxide Sensors. Adv Mater. 2004;16(22):2049-52.
Sun et al., Functionalized Carbon Nanotubes: Properties and Applications. Acc Chem Res. 2002;35(12):1096-1104.
Sun et al., Soluble graphene through edge-selective functionalization. Nano Res. Feb. 2010;3(2):117-125.
Swager et al., Functional graphene: Top-down chemistry of the π-surface. ACS Macro Lett. 2012;1(1):3-5. Epub Nov. 9, 2011.
Swager, The molecular wire approach to sensory signal amplification. Acc Chem Res. 1998;31:201-07.
Tang et al., Measurement of ionizing radiation using carbon nanotube field effect transistor. Phys Med Biol. Feb. 7, 2005;50(3):N23-31.
Tasis et al., Chemistry of Nanotubes. Chem Rev. 2006;106(3):1105-36.
Terrier, Rate and equilibrium studies in Jackson-Meisenheimer complexes. Chem Rev. Apr. 1982;82(2):77-152.
Toal et al., Polymer sensors for nitroaromatic explosives detection. Mater Chem. 2006;16:2871-83.
Tombler et al., Reversible electromechanical characteristics of carbon nanotubes under local-probe manipulation. Nature. 2000;405:769-72.
Volatron et al., Electron transfer properties of a monolayer of hybrid polyoxometalates on silicon. J Mater Chem C. 2015;3:6266-75. Accepted Author Manuscript, 17 pages.
Wang et al., Carbon Nanotube/Polythiophene Chemiresistive Sensors for Chemical Warfare Agents. J Am Chem Soc. 2008;130:5392-93.
Wang et al., High-yield synthesis of few-layer graphene flakes through electrochemical expansion of graphite in propylene carbonate electrolyte. J Am Chem Soc. Jun. 15, 2011;133(23):8888-91. Epub May 17, 2011.
Wang et al., Novel multicomponent reaction of [60]fullerene: the first example of 1,4-dipolar cycloaddition reaction in fullerene chemistry. Org Biomol Chem. 2006;4:4063-64.
Wang et al., Synthesis of enhanced hydrophilic and hydrophobic graphene oxide nanosheets by a solvothermal method. Carbon. Jan. 1, 2009;47(1):68-72.
Webb et al., A simple method to produce almost perfect graphene on highly oriented pyrolytic graphite. Carbon. Aug. 2011;49(10):3242-9. Epub Apr. 3, 2011.
Wei et al., Covalent functionalization of single walled carbon nanotubes and fullerenes via a zwitterion approach. Chemical Abstracts. 2007. 2 pages.
Wei et al., Multifunctional chemical vapor sensors of aligned carbon nanotube and polymer composites. J Am Chem Soc. Feb. 8, 2006;128(5):1412-3.
Weizmann et al., DNA-CNT nanowire networks for DNA detection. J Am Chem Soc. Mar. 16, 2011;133(10):3238-41. Epub Feb. 22, 2011.
Wu et al., Selective surface functionalization at regions of high local curvature in graphene. Chem Commun (Camb). Jan. 25, 2013;49(7):677-9. doi: 10.1039/c2cc36747e. Epub Nov. 29, 2012.
Yates et al., The absorption coefficient spectrum and radiation degradation of poly (butene-1 sulfone) in the soft X-ray region. J Poly Sci Part B Poly Phys. 1993;31:1837-44.
Yoo et al., Enhanced electrocatalytic activity of Pt subnanoclusters on graphene nanosheet surface. Nano Lett. Jun. 2009;9(6):2255-9.
Zaharescu et al., Electrical properties of polyolefin blends under γ-radiation exposure. ICSD 2004. Proceedings of the 2004 Inter National Conference on Solid Dielectrics. Toulouse, France. Jul. 5-9, 2004. IEEE. Jul. 5, 2004;1:367-69.
Zarzar et al., Dynamically reconfigurable complex emulsions via tunable interfacial tensions. Nature. Feb. 26, 2015;518(7540):520-4. doi: 10.1038/nature14168. Suppl Info 8 pages.
Zhang et al., Covalent Functionalization of Singled Walled Carbon Nanotubes and Fullerenes via a Zwitterion Approach. Prep Pap.-Am Chem Soc, Div Fuel Chem. 2007;52(1):126-28.
Zhang et al., Electochemically Functionalized Single-Walled Carbon Nanotube Gas Sensor. Electroanalysis. 2006;18(12):1153-58.
Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.
Zhang et al., Modular Functionalization of Carbon Nanotubes and Fullerenes. J Am Chem Soc. 2009;131:8446-54.
Zhao et al., Synthesis and characterization of water soluble single-walled carbon nanotube graft copolymers. J Am Chem Soc. Jun. 8, 2005;127(22):8197-203.
Zheng et al., Electrochemical intercalation of lithium into a natural graphite anode in quaternary ammonium-based ionic liquid electrolytes. Carbon. Feb. 2006; 44(2):203-210.
Zhong et al., Enhanced electrochemical expansion of graphite for in situ electrochemical functionalization. J Am Chem Soc. Oct. 31, 2012;134(43):17896-9. doi: 10.1021/ja309023f. Epub Oct. 17, 2012.
Zhou et al., A New Method for the Functionalization of [60] Fullerene: An Unusual 1,3-Dipolar Cycloaddition Pathway Leading to a C60 Housane Derivative. Organic Letters. 2005;7(26):5849-51.
Zhu et al., Covalent Functionalization of Surfactant-Wrapped Graphene Nanoribbons. Chemistry of Materials. 2009;21:5284-91.
International Search Report and Written Opinion dated Feb. 7, 2019 for Application No. PCT/US2018/059422.
Dobson et al., How many-body effects modify the van der Waals interaction between graphene sheets. Phys Rev X. May 2014;4(2):021040(1-9).
El-Gendy et al, Adenine-functionalized spongy graphene for green and high-performance supercapacitors. Sci Reports. Feb. 20, 2017;7:43104(1-10).
Jeon, Synthesis of Functionalized Few Layer Graphene via Electrochemical Expansion. Master's Thesis. Massachusetts Institute of Technology, Department of Materials Science and Engineering. Submitted Feb. 2015. Abstract, Chpt 2 and portion of Chpt 3, pp. 24-42, 23 pages.
Leroux et al., Synthesis of functionalized few-layer graphene through fast electrochemical expansion of graphite. J Electroanal Chem Interfacial Electrochem. Sep. 2015;753:42-6. Accepted author manuscript, 16 pages.
Sablok et al., Amine functionalized graphene oxide/CNT nanocomposite for ultrasensitive electrochemical detection of trinitrotoluene. J Hazard Mater. Mar. 15, 2013;248-249:322-8.
Bekyarova et al., Chemical modification of epitaxial graphene: Spontaneous grafting of aryl groups. J Am Chem Soc. 2009;131:1336-7. Epub Jan. 9, 2009.
Zarzar et al., Dynamically reconfigurable complex emulsions via tunable interfacial tensions. Nature. Feb. 26, 2015;518(7540):520-4. Author Manuscript, 20 pages.

\* cited by examiner

HIGH FUNCTIONALIZATION DENSITY GRAPHENE

RELATED APPLICATIONS

This application claims priority under 35 U.S.C. § 119(e) to U.S. Provisional Application No. 62/582,074, filed Nov. 6, 2017, and entitled "High Functionalization Density Graphene", which is incorporated herein by reference in its entirety and for all purposes.

FEDERALLY SPONSORED RESEARCH

This invention was made with Government support under DMR-1410718 awarded by the National Science Foundation. The Government has certain rights in the invention.

TECHNICAL FIELD

Systems and methods associated with carbon-based materials, such as functionalized graphene, are generally described.

BACKGROUND

Carbon-based materials may be beneficially employed in a variety of applications. However, it is often challenging to obtain carbon-based materials in a desirable state. For instance, it may be difficult to obtain fully exfoliated, unaggregated graphene from graphite and to obtain graphene with desirable chemical functionalization.

Accordingly, improved articles and methods are needed.

SUMMARY

Articles and methods related to carbon-based materials, such as functionalized graphene, are generally described. The subject matter of the present invention involves, in some cases, interrelated products, alternative solutions to a particular problem, and/or a plurality of different uses of one or more systems and/or articles.

In some embodiments, a carbon-based material is provided. The carbon-based material comprises a carbon-based portion and a functional group bonded to the carbon-based portion. The functional group is capable of forming a reversible covalent bond with a species. Carbon makes up greater than or equal to 30 wt % of the carbon-based portion.

In some embodiments, a carbon-based material is provided. The carbon-based material comprises graphene comprising a plurality of carbon atoms and a plurality of functional groups bonded to the graphene. A ratio of a total number of functional groups in the plurality of functional groups to a total number of carbon atoms in the plurality of carbon atoms of the graphene is greater than or equal to 1:50.

In some embodiments, a carbon-based material is provided. The carbon-based material comprises a plurality of graphene sheets. Greater than or equal to 70% of the graphene sheets are spaced apart from their nearest neighbors by a distance of greater than or equal to 10 Å.

In some embodiments, a method is provided. The method comprises applying a voltage to a carbon-based material in the presence of a combination of solvents. The combination of solvents comprises a solvent stable at voltages of greater than or equal to −3.15 V and less than or equal to −2.2 V. The combination of solvents comprises a solvent with a surface tension within 25% of a surface tension of the carbon-based material.

In some embodiments, a method is provided. The method comprises applying a decreasing voltage to a carbon-based material. The decreasing voltage decreases at a rate of greater than or equal to 2 µV/s and less than or equal to 40 µV/s. The decreasing voltage has a value of greater than or equal to −2.2 V and less than or equal to −3.15 V at at least one point in time.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
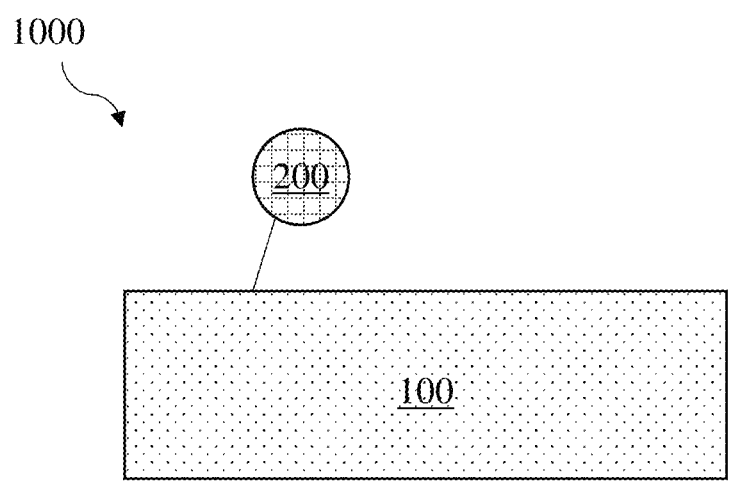
FIG. 1A is a schematic depiction of a carbon-based material comprising a functional group, in accordance with some embodiments.

Carbon-based materials, methods of forming carbon-based materials, and associated articles and methods are generally provided. Some embodiments relate to carbon-based materials comprising functional groups that are particularly advantageous. For instance, some carbon-based materials described herein comprise functional groups that are capable of forming reversible covalent bonds with a species. The reversible covalent bonds may desirably allow the carbon-based material to bind with species of particular utility. For instance, the reversibly-bonded species may be a species that is particularly desirable to sense and/or a species that is particularly desirable to reversibly bond to the carbon-based material. In the former case, the species may be sensed upon forming a reversible covalent bond with the carbon-based material. In the latter case, a reversible covalent bond may be formed between the species and the carbon-based material, localizing the species thereon for the duration of time that the reversible covalent bond is formed. In some embodiments, a reversible covalent bond may be desirable for applications in which it would be beneficial for the carbon-based material to exhibit self-healing, such as stretchable graphene applications and/or superlubricant tribofilm applications. In some embodiments, a carbon-based material described herein comprises a relatively high density of functional groups. This may be advantageous for, for example, bonding large amounts of desirable species. In some embodiments, a high density of functional groups may suppress aggregation of the carbon-based material.

Some carbon-based materials described herein have morphologies that are particularly desirable. For example, a carbon-based material may comprise a plurality of graphene sheets that are spaced apart from their nearest neighbors by a relatively large amount. In some embodiments, a relatively large portion of the graphene sheets in the plurality of graphene sheets may be spaced apart from their nearest neighbors by a relatively large amount. Without wishing to be bound by any particular theory, it is believed that graphene sheets that are spaced apart to a relatively high degree may be particularly facile to functionalize and/or to separate from each other. Accordingly, a plurality of graphene sheets that comprises a high proportion of relatively highly spaced apart graphene sheets may be particularly desirable as intermediates for forming highly functionalized and/or highly dispersed graphene.

Some embodiments relate to methods of forming carbon-based materials. A method may comprise applying a voltage to a carbon-based material in a manner that promotes the formation of a desirable morphology, such as a morphology comprising a plurality of graphene sheets that are spaced apart from their nearest neighbors by a relatively large amount. The voltage may be applied in the presence of particularly advantageous solvents, such as solvents that promote intercalation of species (e.g., ions of opposite charge to the voltage applied) between the graphene sheets. In some embodiments, the voltage applied to the carbon-based material may be selected to promote a desirable result. For instance, the voltage may be applied for a duration and/or at a magnitude that promotes the desirable intercalation of species within the carbon-based material (e.g., between graphene sheets therein). As another example, the magnitude and/or manner in which the voltage is applied, such as the ramp rate of the voltage, may be relatively mild. The intercalation of a species under relatively mild conditions may advantageously result in the introduction of relatively few impurities into the carbon-based material during the intercalation process and/or may advantageously cause the carbon-based material to exhibit relatively little degradation during the intercalation process.

Figure 1B:
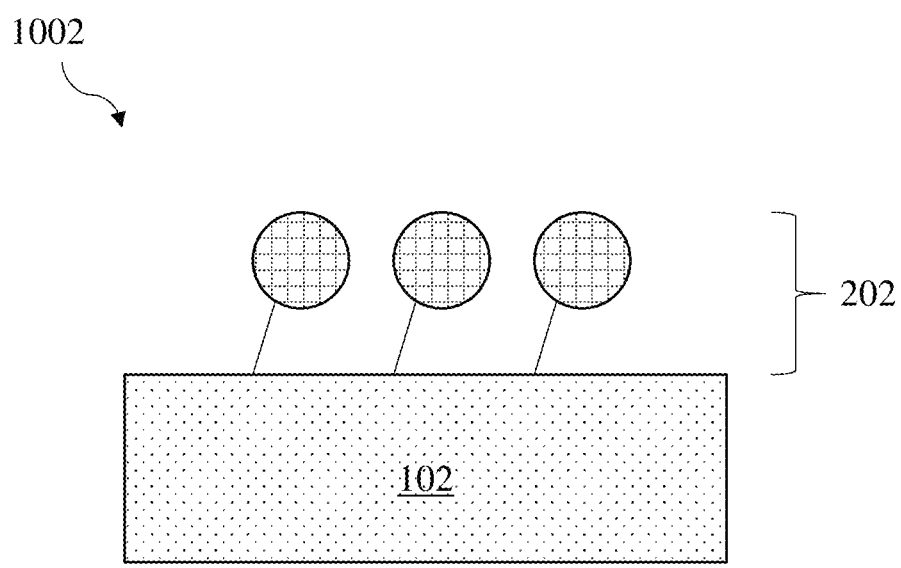
FIG. 1B is a schematic depiction of a carbon-based material comprising a plurality of functional groups, in accordance with some embodiments.

As also described above, some embodiments relate to carbon-based materials. The carbon-based materials may comprise a carbon-based portion and a functional group bonded to the carbon-based portion. FIG. 1A shows one example of a carbon-based material 1000 comprising a carbon-based portion 100 and a functional group 200 bonded to the carbon-based portion. The functional group may be bonded to the carbon-based portion in a variety of suitable methods, such as by covalent bonding. In some embodiments, a carbon-based material comprises a plurality of functional groups. FIG. 1B shows one example of a carbon-based material 1002 comprising a carbon-based portion 102 and a plurality of functional groups 202 bonded to the carbon-based portion. When present, the plurality of functional groups may include functional groups of only a single type, or may comprise more than one type of functional group.

It should be understood that some pluralities of functional groups, like the plurality shown in FIG. 1B, may be bonded to a single surface of a carbon-based portion of a carbon-based material. In other embodiments, functional groups in a plurality of functional groups may be bonded to more than one, or all, of the surfaces of the carbon-based portion of the carbon-based material. When a plurality of functional groups is bonded to more than one surface of the carbon-based portion, each surface of the carbon-based portion may be bonded to functional groups of substantially similar type and at a substantially similar density, two or more surfaces of the carbon-based portion may be bonded to functional groups of different types and/or different densities, and/or each surface may be bonded to functional groups of different types and at different densities.

Functional groups bonded to a surface of a carbon-based portion of a carbon-based material may be bonded to the surface of the carbon-based portion in a variety of suitable manners. In some embodiments, the functional groups may be bonded to the surface of the carbon-based portion in a relatively uniform manner. In other words, the density of the bonded functional groups across the surface of the carbon-based portion may be relatively constant. In some embodiments, the functional groups may be bonded to the surface of the carbon-based portion in a manner that is not uniform. For instance, some portions of the surface of the carbon-based material may be bonded to clusters of functional groups and/or the density of the bonded functional groups may be higher in some portions of the surface of the carbon-based portion than in others. As another example, some portions of the surface of the carbon-based portion may be bonded to functional groups and some portions of the surface may not be bonded to functional groups.

Figure 2:
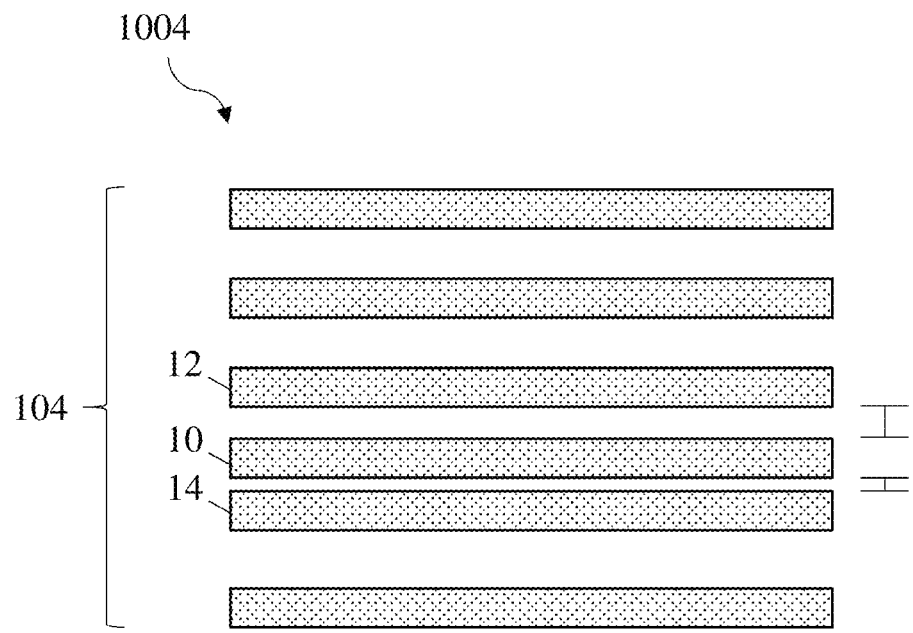
FIG. 2 is a schematic depiction of a carbon-based material, in accordance with some embodiments.

As also described above, some embodiments relate to carbon-based materials comprising a plurality of graphene sheets positioned with respect to each other in an advantageous manner. In some embodiments, the graphene sheets are positioned with respect to each other such that a relatively large portion of the graphene sheets are spaced a relatively large distance from their nearest neighbors. FIG. 2 shows one example of a carbon-based material 1004 comprising a plurality of graphene sheets 104. The plurality of graphene sheets 104 comprises a graphene sheet 10 having a nearest neighbor 12 and a nearest neighbor 14. The graphene sheet 10 is spaced apart from its nearest neighbor 12 by a spacing 22 and is spaced apart from its nearest neighbor 14 by a spacing 24. In some embodiments, as shown in FIG. 2, a plurality of graphene sheets may comprise graphene sheets that are spaced apart from their nearest neighbors by differing amounts. A plurality of graphene sheets may comprise graphene sheets that are spaced apart from their nearest neighbors by different amounts, but for which all or a large portion are spaced apart from their nearest neighbors by at least a certain minimum amount. In other words, a plurality of graphene sheets may comprise graphene sheets that are spaced apart from each other in relatively high, but varying, amounts. In some embodiments, a plurality of graphene sheets comprises graphene sheets that are spaced apart from their nearest neighbors by relatively constant amounts (i.e., graphene sheets that are uniformly spaced). Such graphene sheets may also be spaced apart from each other by at least a certain minimum amount and/or by relatively high amounts.

In some embodiments, methods are provided. A method may comprise applying a voltage to a carbon-based material. The voltage may cause a species to intercalate into the carbon-based material. By way of example, the voltage may cause the carbon-based material to become charged, which may cause the carbon-based material to expand due to electrostatic repulsion. As the carbon-based material expands, one or more species may intercalate therein, causing further expansion of the carbon-based material. In some embodiments, the species intercalating into the carbon-based material comprises ions of opposite charge to the carbon-based material under the applied voltage. These ions may be electrostatically attracted to the charged carbon-based material.

Figure 3A:
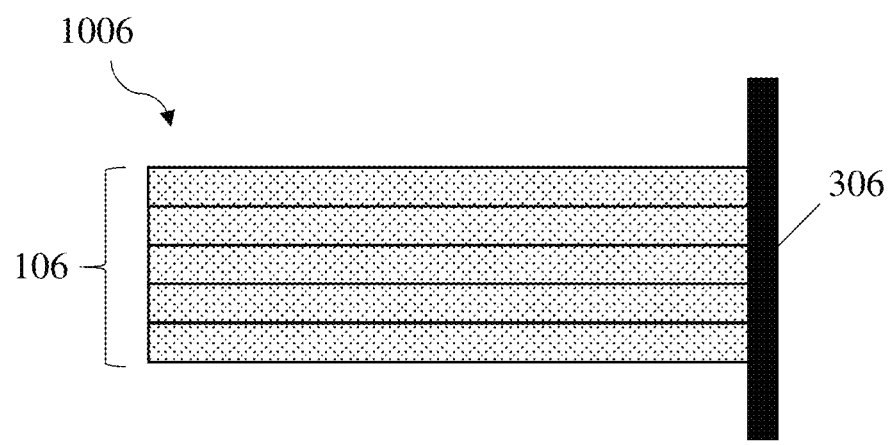
FIGS. 3A-3B are schematic depictions of a method of applying a voltage to a carbon-based material, in accordance with some embodiments.
Figure 3B:
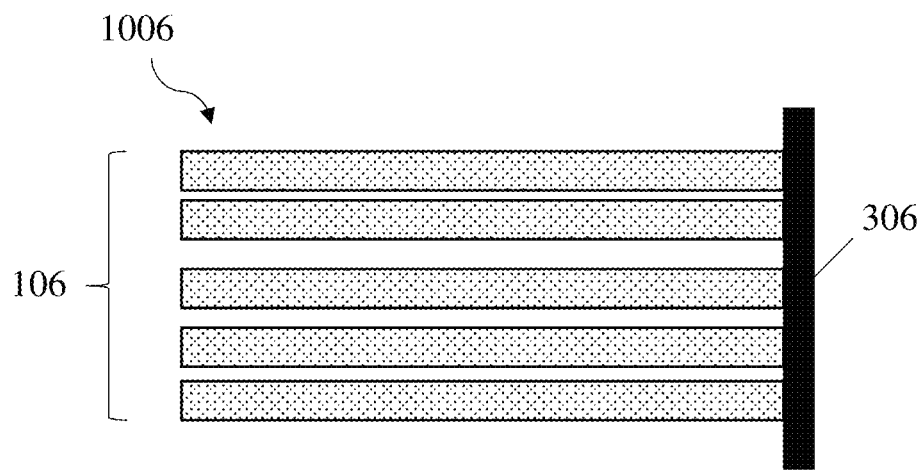

FIGS. 3A-3B depict one example of a method that comprises applying a voltage to a carbon-based material. In FIG. 3A, a voltage is applied to a carbon-based material 1006 by an electrode 306. FIG. 3B shows the carbon-based material 106 after the voltage has been applied for a period of time. As shown in FIG. 3B, application of the voltage from the electrode 306 to the carbon-based material 106 caused the carbon-based material 106 to expand. In some embodiments, like the embodiment shown in FIGS. 3A-3B, the carbon-based material comprises a plurality of graphene sheets (shown as 106 in FIGS. 3A-3B). In some embodiments, the carbon-based material to which the voltage is applied lacks graphene sheets and/or comprises both graphene sheets and another type of carbon-based material.

In some embodiments, a voltage is applied to a carbon-based material that causes the carbon-based material to become functionalized. The voltage may be a voltage that also causes intercalation of a species into the carbon-based material. By way of example, a voltage may both cause intercalation of a species into the carbon-based material and cause the carbon-based material to become functionalized. In some embodiments, a voltage may cause a species functionalizing the carbon-based material to intercalate into the carbon-based material and to react with the carbon-based material to functionalize it (e.g., by an electrochemical grafting reaction). In some embodiments, a voltage may cause a species reactive with the carbon-based material to intercalate into the carbon-based material, and the species reactive with the carbon-based material may spontaneously react with the carbon-based material once intercalated therein. The voltage causing the carbon-based material to become functionalized may be applied to a carbon-based material that has been expanded by application of a voltage (e.g., a carbon-based material having a morphology similar to that shown in FIG. 3B) and/or to a carbon-based material that has not been expanded by application of a voltage.

As described above, in some embodiments, a carbon-based material comprises a functional group bonded to a carbon-based portion. The functional group may be present in a relatively high amount. For instance, the carbon-based material may comprise a carbon-based portion (e.g., graphene) comprising a plurality of carbon atoms and a plurality of functional groups, and a ratio of the total number of functional groups in the plurality of functional groups to a total number of carbon atoms in the plurality of carbon atoms of the graphene may be greater than or equal to 1:50, greater than or equal to 1:45, greater than or equal to 1:40, greater than or equal to 1:35, greater than or equal to 1:30, greater than or equal to 1:25, greater than or equal to 1:20, greater than or equal to 1:15, or greater than or equal to 1:12. The ratio of the total number of functional groups in the plurality of functional groups to a total number of carbon atoms in the plurality of carbon atoms of the graphene may be less than or equal to 1:10, less than or equal to 1:12, less than or equal to 1:15, less than or equal to 1:20, less than or equal to 1:25, less than or equal to 1:30, less than or equal to 1:35, less than or equal to 1:40, or less than or equal to 1:45. Combinations of the above-referenced ranges are also possible (e.g., greater than or equal to 1:50 and less than or equal to 1:10, or greater than or equal to 1:12 and less than or equal to 1:10). Other ranges are also possible. When the plurality of functional groups includes two or more types of functional groups, the ranges described above may refer to the total amount of functional groups making up the plurality of functional groups, or to the total amount of any particular type of functional group in the plurality of functional groups.

Without wishing to be bound by any particular theory, it is believed that high functionalization densities of graphene may be particularly desirable because they may promote dispersion of graphene in one or more solvents and/or may suppress aggregation of graphene in one or more solvents. The presence of functional groups on one or more surfaces of a graphene sheet may increase the minimum distance it may be positioned from another graphene sheet. In other words, two graphene sheets that are functionalized may not be able to approach each other as closely as unfunctionalized graphene sheets because the functional groups will also be positioned therebetween. Increased spacing between the graphene sheets may weaken their van der Waals interactions, and reduce their tendency to aggregate. In some embodiments, graphene with high functionalization densities may desirably be capable of being deposited on a substrate as single layer graphene and/or double layer graphene. It is believed that the functional groups may reduce the extent to which the graphene can organize into ordered structures when deposited from solution and/or may prevent graphene from organizing into ordered structures for similar reasons to those described above with respect to graphene aggregation in solution. In some embodiments, a high functionalization density causes turbostratic graphene to form.

As described above, in some embodiments, a carbon-based material comprises a functional group capable of forming a reversible covalent bond. As used herein, a reversible covalent bond is a bond that can be formed, broken, and then reformed. In some embodiments, a reversible covalent bond can undergo a cycle in which it is formed (or reformed) and broken at least 2 times, at least 3 times, at least 4 times, at least 5 times, at least 10 times, at least 20 times, at least 50 times, or at least 100 times. In some embodiments, it is possible to break the reversible covalent bond in a manner such that the functional group initially forming the reversible covalent bond is not altered in a way that detracts from its ability to reform the reversible covalent bond. In some embodiments, it is possible to break the reversible covalent bond in a manner such that the species forming the reversible covalent bond with the functional group is not altered in a way that detracts from its ability to reform the reversible covalent bond. It may be possible to break the reversible covalent bond such that the functional group, the carbon-based material, and/or the species forming the reversible covalent bond with the functional group are not altered except for the breaking of the reversible covalent bond.

Some functional groups may be capable of forming reversible covalent bonds under conditions that are relatively mild. For instance, in some embodiments, a carbon-based material comprises a plurality of functional groups capable of forming and/or breaking a reversible covalent bond at a temperature of greater than or equal to 5° C., greater than or equal to 10° C., greater than or equal to 15° C., greater than or equal to 20° C., greater than or equal to 25° C., greater than or equal to 30° C., greater than or equal to 35° C., greater than or equal to 40° C., greater than or equal to 45° C., greater than or equal to 50° C., greater than or equal to 60° C., greater than or equal to 65° C., or greater than or equal to 70° C. In some embodiments, a carbon-based material comprises a plurality of functional groups capable of forming and/or breaking a reversible covalent bond at a temperature of less than or equal to 75° C., less than or equal to 70° C., less than or equal to 65° C., less than or equal to 60° C., less than or equal to 55° C., less than or equal to 50° C., less than or equal to 45° C., less than or equal to 40° C., less than or equal to 35° C., less than or equal to 30° C., less than or equal to 25° C., less than or equal to 20° C., less than or equal to 15° C., or less than or equal to 10° C. Combinations of the above-referenced ranges are also possible (e.g., greater than or equal to 5° C. and less than or equal to 75° C., or greater than or equal to 10° C. and less than or equal to 30° C.). Other ranges are also possible.

In some embodiments, a carbon-based material comprises a plurality of functional groups capable of forming and/or breaking a reversible covalent bond at a pressure of close to atmospheric pressure. The carbon-based material may comprise a plurality of functional groups capable of forming and/or breaking a reversible covalent bond at a pressure of greater than or equal to 0.75 atm, greater than or equal to 0.8 atm, greater than or equal to 0.85 atm, greater than or equal to 0.9 atm, greater than or equal to 0.95 atm, greater than or equal to 1 atm, greater than or equal to 1.05 atm, greater than or equal to 1.1 atm, greater than or equal to 1.15 atm, or greater than or equal to 1.2 atm. The carbon-based material may comprise a plurality of functional groups capable of forming and/or breaking a reversible covalent bond at a pressure of less than or equal to 1.25 atm, less than or equal to 1.2 atm, less than or equal to 1.15 atm, less than or equal to 1.1 atm, less than or equal to 1.05 atm, less than or equal to 1 atm, less than or equal to 0.95 atm, less than or equal to 0.9 atm, less than or equal to 0.85 atm, or less than or equal to 0.8 atm. Combinations of the above-referenced ranges are also possible (e.g., greater than or equal to 0.75 atm and less than or equal to 1.25 atm). Other ranges are also possible.

In some embodiments, the plurality of functional groups may be capable of forming and/or breaking a reversible covalent bond at both a pressure and temperature within the above-referenced ranges (e.g., at a pressure of greater than or equal to 0.75 atm and less than or equal to 1.25 atm and a temperature of greater than or equal to 5° C. and less than or equal to 75° C.).

In some embodiments, a carbon-based material comprises a plurality of functional groups capable of forming and/or breaking a reversible covalent bond with a relatively low amount of energy input. By way of example, the carbon-based material may comprise a plurality of functional groups capable of forming and/or breaking a reversible covalent bond with an energy input ~$k_B T$. The carbon-based material may comprise a plurality of functional groups capable of forming and/or breaking a reversible covalent bond with an energy input of greater than or equal to 0.75 $k_B T$, greater than or equal to 0.8 $k_B T$, greater than or equal to 0.85$k_B T$, greater than or equal to 0.9 $k_B T$, greater than or equal to 0.95 $k_B T$, greater than or equal to $k_B T$, greater than or equal to 1.05 $k_B T$, greater than or equal to 1.1 $k_B T$, greater than or equal to 1.15 $k_B T$, or greater than or equal to 1.2 $k_B T$. The carbon-based material may comprise a plurality of functional groups capable of forming and/or breaking a reversible covalent bond with an energy input of less than or equal to 1.25 $k_B T$, less than or equal to 1.2 $k_B T$, less than or equal to 1.15 $k_B T$, less than or equal to 1.1 $k_B T$, less than or equal to 1.05 $k_B T$, less than or equal to $k_B T$, less than or equal to 0.85 $k_B T$, or less than or equal to 0.8 $k_B T$. Combinations of the above-referenced ranges are also possible (e.g., greater than or equal to 0.75 $k_B T$ and less than or equal to 1.25 $k_B T$).

Other ranges are also possible. In the above-referenced ranges, T may be one or more of the temperatures described above (e.g., greater than or equal to 5° C. and less than or equal to 75° C.).

In some embodiments, a reversible covalent bond is capable of being broken and/or formed in a dynamic process. In other words, it may be possible to break and form some reversible covalent bonds in the same environment. By way of example, a carbon-based material comprising a plurality of functional groups may be positioned in an environment in which some of the functional groups are capable of forming reversible covalent bonds and in which some functional groups of the same type are capable of breaking a reversible covalent bond. In other embodiments, a reversible covalent bond is capable of being formed in an environment in which it is not capable of being broken (or not capable of being broken in a reversible manner) and/or is capable of being broken in an environment in which it is not capable of being formed (or not capable of being broken in a reversible manner).

Non-limiting examples of suitable reversible covalent bonds include covalent bonds bonding together a nucleophile and an aromatic carbon in a Meisenheimer complex, covalent bonds between activated carbonyl groups and amine groups, covalent bonds between diol groups and boronic acid groups, covalent bonds between carboxylic acid groups and boronic acid groups, and covalent bonds between dienophile groups and diene groups formed by Diels-Alder reactions.

Figure 4:
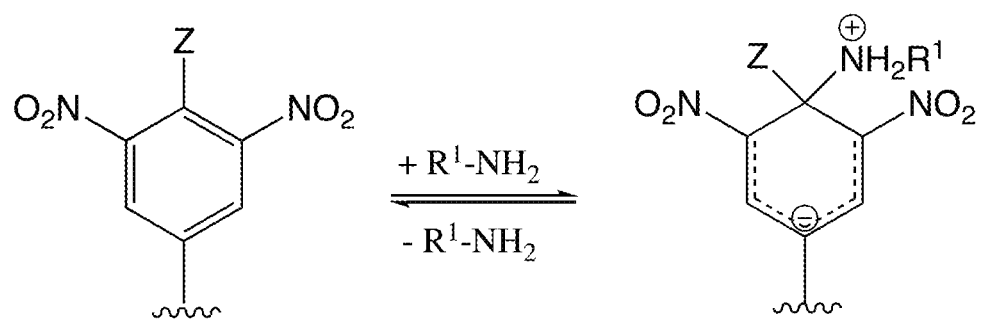
FIG. 4 is a schematic depiction of the formation of a Meisenheimer complex, in accordance with some embodiments.

In some embodiments, a functional group capable of forming a reversible covalent bond comprises a functional group capable of forming a Meisenheimer complex. FIG. 4 shows a schematic depiction of the formation of a Meisenheimer complex between a 3,5-dinitrophenyl group and a species comprising a primary amine group. Other types of Meisenheimer complexes are also contemplated. Non-limiting examples of suitable functional groups capable of forming a Meisenheimer complex include: a functional group comprising an aromatic portion; a functional group comprising a nitro group; and a functional group comprising a sulfonyl group, such as a sulfonyl group covalently bonded to an electron-withdrawing group (e.g., a sulfonyl group covalently bonded to a $CF_3$ group). Some functional groups capable of forming Meisenheimer complexes may comprise two or more of the above types of functional groups. For instance, a functional group capable of forming a Meisenheimer complex may comprise both an aromatic portion and a group capable of stabilizing the negative charge added to the aromatic portion when the Meisenheimer complex is formed, such as a functional group comprising an aromatic portion and a nitro group (e.g., a 3,5-dinitrophenyl group) and/or a functional group comprising an aromatic portion and a sulfonyl group (e.g., a functional group comprising an aromatic portion and a such as a sulfonyl group covalently bonded to an electron-withdrawing group, such as $CF_3$ group).

Further non-limiting examples of functional groups capable of forming a Meisenheimer complex include the following:

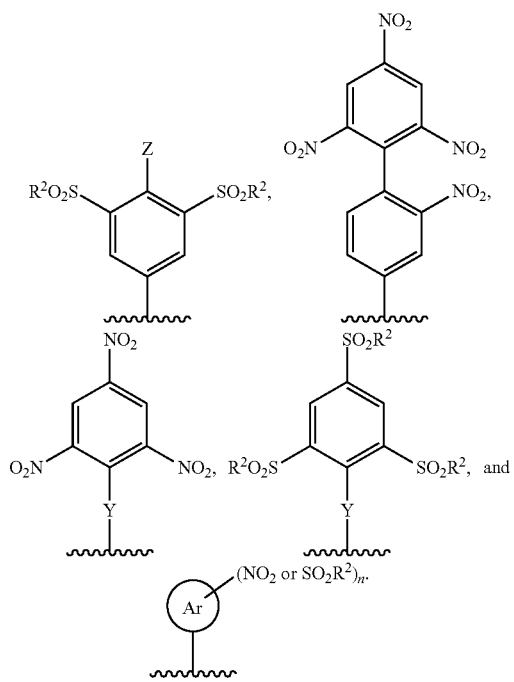

For each of the structures shown above, each $R^2$, Y, and Z may independently be hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, nitro, optionally substituted sulfonyl, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile.

Non-limiting examples of suitable species that may be capable of reacting with one or more of the above-referenced functional groups to form a Meisenheimer complex include molecules comprising a nucleophilic group, such as an amine group. For instance, the species may comprise a primary amine group (e.g., n-butyl amine), a secondary amine group, and/or a tertiary amine group. Additional features of species capable of bonding with functional groups will be described in further detail below.

Figure 5:
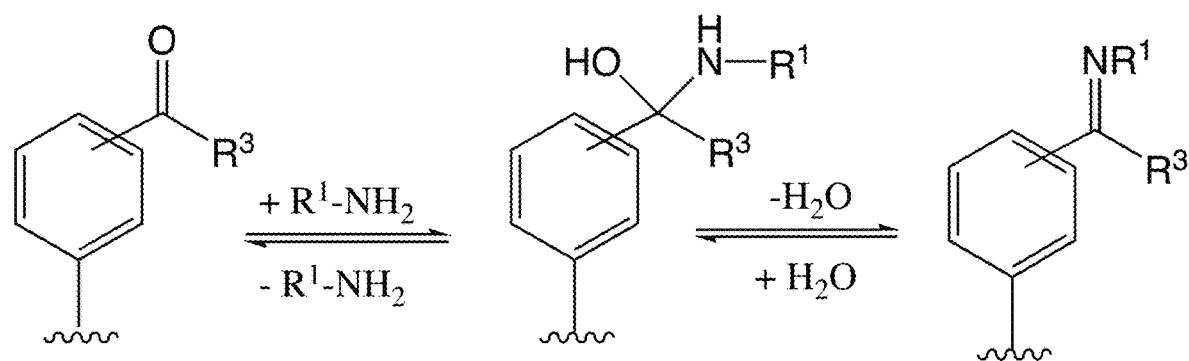
FIG. 5 is a schematic depiction of the formation of a reversible covalent bond between a functional group comprising an activated carbonyl group and a species comprising a primary amine group, in accordance with some embodiments.

In some embodiments, a functional group capable of forming a reversible covalent bond comprises an activated carbonyl group. FIG. 5 shows a schematic depiction of the formation of a reversible covalent bond between a functional group comprising an activated carbonyl group and a species comprising a primary amine group. FIG. 5 also shows the reversible formation of an imine group by reaction of the species comprising the reversible covalent bond with water. It should be understood that some reversible covalent bonds formed between a functional group comprising an activated carbonyl group and an amine group contemplated herein may not be capable of reaction with water to form an imine group and/or may be capable (or not) of reacting with a species other than water (e.g., a species comprising an alcohol group) to form an imine group. It should also be understood that reversible covalent bonds formed between other types of functional groups comprising activated carbonyl groups and other types of species (e.g., other types of amine groups) are also contemplated.

Non-limiting examples of suitable functional groups comprising activated carbonyl groups include: a functional group comprising an aromatic portion, a functional group comprising an aldehyde group, a functional group comprising a ketone group (e.g., a ketone group activated by an electron-withdrawing group), a functional group comprising a fluorinated group in the alpha position (e.g., a —CFR$^1$R$^2$ group, a —CF$_2$R$^1$ group, a —CF$_3$ group, a fluorinated alkyl group comprising two or more carbons), a functional group comprising a carbonyl group adjacent to a sulfonyl group, and a functional group comprising a carbonyl group adjacent to another carbonyl group. Some functional groups capable of forming a reversible covalent bond and comprising a carbonyl group may comprise two or more of the above types of functional groups. For instance, a functional group capable of forming a reversible covalent bond and comprising a carbonyl group may comprise both an aromatic portion and an aldehyde group, both an aromatic portion and a ketone group, both an aromatic portion and a carbonyl group adjacent to a sulfonyl group, and/or both an aromatic portion and a carbonyl group adjacent to another carbonyl group.

Further non-limiting examples of functional groups comprising an activated carbonyl group include the following:

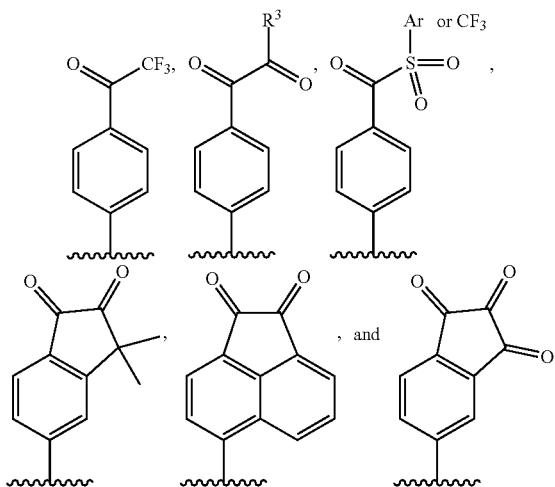

For each of the structures shown above, each R$^3$ may independently be hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, nitro, optionally substituted sulfonyl, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile.

Non-limiting examples of suitable species that may be capable of reacting with one or more of the above-referenced functional groups comprising an activated carbonyl group include molecules comprising a nucleophilic group, such as an amine group. For instance, the species may comprise a primary amine group, a secondary amine group, and/or a tertiary amine group. Additional features of species capable of bonding with functional groups will be described in further detail below.

Figure 6:
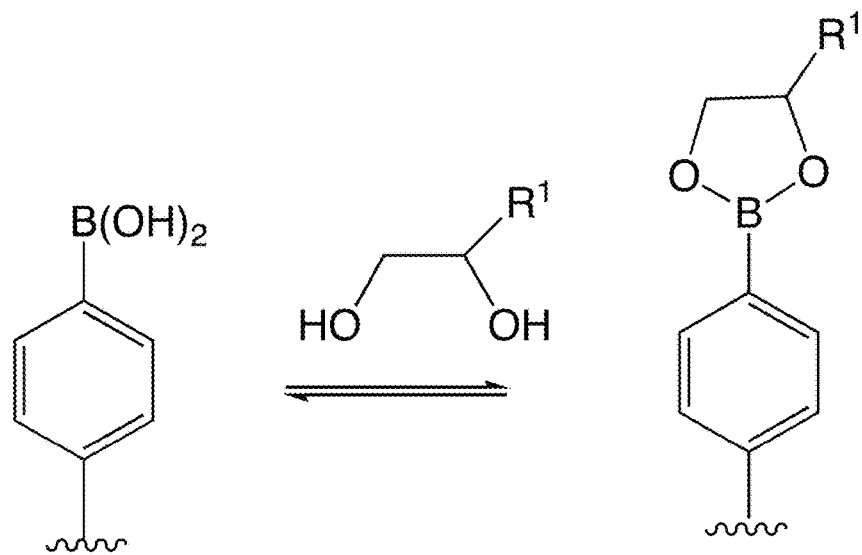
FIG. 6 is a schematic depiction of the formation of a reversible covalent bond between a boronic acid group and a species comprising a 1,2-diol group, in accordance with some embodiments.

In some embodiments, a functional group capable of forming a reversible covalent bond comprises a boronic acid group. FIG. 6 shows a schematic depiction of the formation of a reversible covalent bond between a boronic acid group and a species comprising a 1,2-diol group. In some embodiments, like the embodiment shown in FIG. 6, a functional group capable of forming a reversible covalent bond and comprising a boronic acid group further comprises an aromatic portion. One further example of a functional group comprising a boronic acid group is shown below:

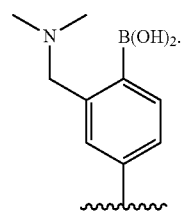

Figure 7:
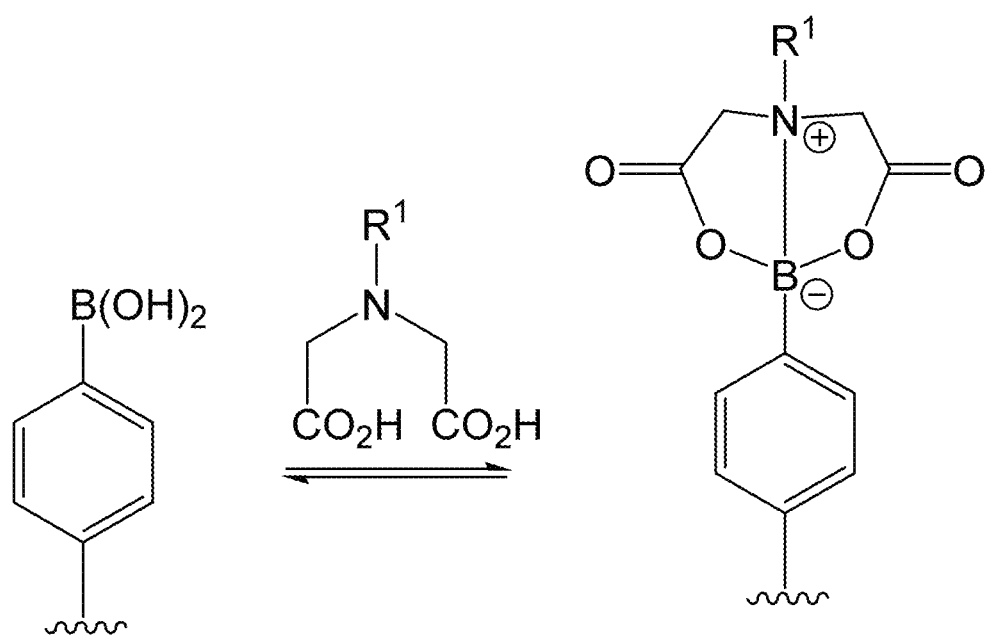
FIG. 7 is a schematic depiction of the formation of a reversible covalent bond between a boronic acid group and a species comprising a dicarboxylic acid group, in accordance with some embodiments.

Non-limiting examples of suitable species that may be capable of reacting with one or more of the above-referenced functional groups comprising a boronic acid group include nucleophiles, such as Lewis bases. The species may comprise a thiol group, a diol group, and/or a dicarboxylic acid group. In some embodiments, the species comprises a 1,2-diol group (e.g., 1,2-benzene diol), a 1,3-diol group, and/or another suitable type of diol group. In some embodiments, the species is a molecule comprising a carboxylic acid group, such as a molecule comprising a dicarboxylic acid group and an amine group (e.g., an amine group in the alpha position). FIG. 7 shows a schematic depiction of the formation of a reversible covalent bond between a boronic acid group and a species comprising a dicarboxylic acid group. Some species comprising a dicarboxylic acid group, like the species shown in FIG. 7, also comprise a tertiary amine group positioned between the two carboxylic acid groups. Other species comprising a dicarboxylic acid group may lack tertiary amine groups and/or other amine groups positioned between the two carboxylic acid groups.

For the species shown in FIG. 7, each R$^1$ may independently be hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, nitro, optionally substituted sulfonyl, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile.

Figure 8:
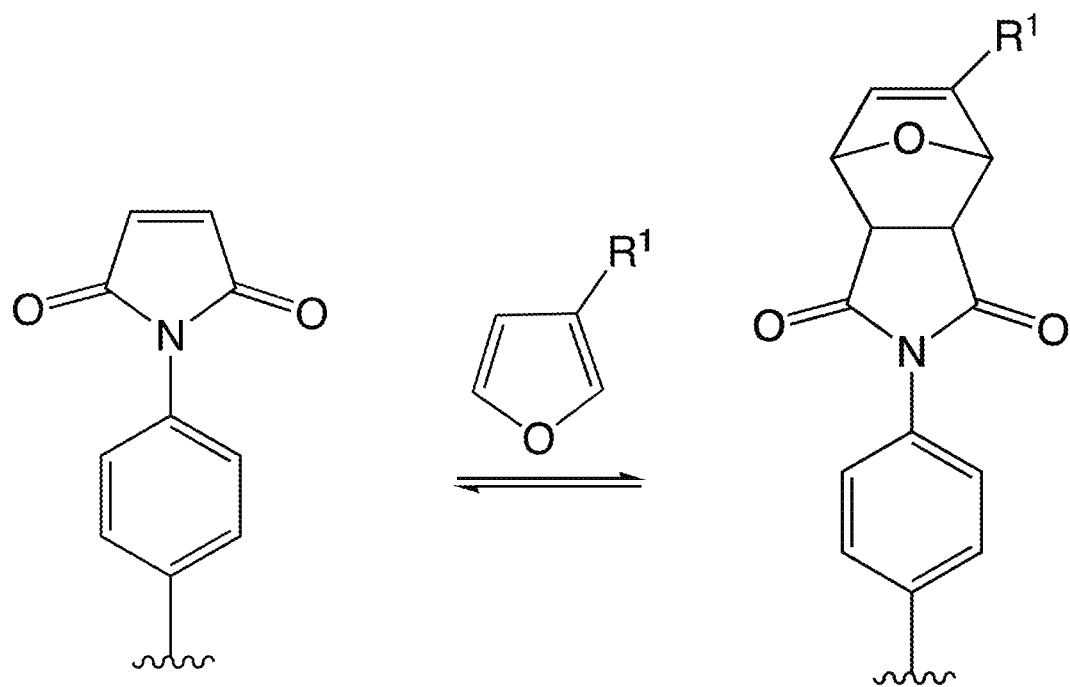
FIG. 8 is a schematic depiction of the formation of a reversible covalent bond by a Diels-Alder reaction, in accordance with some embodiments.

In some embodiments, a functional group capable of forming a reversible covalent bond comprises a functional group capable of undergoing a Diels-Alder reaction. FIG. 8 shows a schematic depiction of the formation of a reversible covalent bond by a Diels-Alder reaction. For the species shown in FIG. 8, each R$^1$ may independently be hydrogen, optionally substituted alkyl, alcohol, halo, optionally substituted heteroalkyl, optionally substituted cycloheteroalkyl, optionally substituted alkenyl, optionally substituted alkynyl, optionally substituted aryl, optionally substituted heteroaryl, optionally substituted alkenyloxy, optionally substituted alkoxy, optionally substituted thio, epoxy, nitro, optionally substituted sulfonyl, optionally substituted acyl, optionally substituted oxyacyloxy, optionally substituted aminoacyl, azide, optionally substituted amino, optionally substituted phosphine, optionally substituted sulfide, isonitrile, cyanate, isocynanate, or nitrile.

In some embodiments, like the embodiment shown in FIG. 8, a functional group capable of undergoing a Diels-Alder reaction comprises a diene group and may be capable of reacting with a species comprises a dienophile group to form a reversible covalent bond. However, in other embodiments, the functional group may comprise a dienophile group and may be capable of reacting with a species comprising a diene group to form a reversible covalent bond. One non-limiting example of a suitable diene group is a maleimide group. One non-limiting example of a suitable dienophile group is a furan group.

A variety of suitable species may be capable of reacting with a functional group to form a reversible covalent bond. In some embodiments, the species, in addition to comprising one or more of the groups described above, may have utility for one or more applications. Accordingly, the carbon-based materials described herein may have utility for forming reversible covalent bonds with species of particular technological interest. Such carbon-based materials may be employed to sense the relevant species. For instance, the carbon-based material may bind to a technologically relevant species that itself is capable of bonding to a fluorescent emitter. When the fluorescent emitter binds to the bound species, its emission may be quenched, indicating the presence of the bound species.

In some embodiments, a carbon-based material reversibly bonded to a species may provide the species to a location and/or environment where it has desirable functionality. By way of example, a carbon-based material reversibly bonded to a species that has barrier properties may be positioned in an environment in which barrier properties are desirable. As another example, a carbon-based material reversibly bonded to a species that suppresses corrosion and/or fouling may be positioned on an electrode in which corrosion and/or fouling is undesirable. As a third example, a carbon-based material reversibly bonded to a species that is biocompatible may be positioned in a location where biocompatibility is desirable.

In some embodiments, a carbon-based material may be capable of bonding with a species that causes the carbon-based material to be localized to a particularly desirable location. For instance, a carbon-based material may be capable of bonding with a species employed as a surfactant that stabilizes an emulsion. The carbon-based material may desirably be localized to the interface between the oil and the water in the emulsion due to exchange reactions with the surfactant. In some embodiments, a carbon-based material localized at such an interface may stabilize the emulsion.

Species capable of bonding with the functional groups described herein may have a variety of suitable forms. Some embodiments relate to species capable of bonding with the functional groups described herein that are small molecules, and some embodiments relate to species capable of bonding with the functional groups described herein that are polymers. Some embodiments relate to species capable of bonding with the functional groups described herein that are synthetic molecules, and some embodiments relate to species capable of bonding with the functional groups described herein partners that are natural molecules (e.g., biological molecules). Non-limiting examples of suitable species capable of bonding with the functional groups described herein include proteins (e.g., enzymes), polynucleotides (e.g., DNA, RNA), catalysts, three-dimensional scaffolds, sugars, cellulose, and wood.

As described above, the carbon-based materials described herein, may comprise a carbon-based portion. The carbon-based portion may comprise carbon in a relatively high amount. Carbon may make up greater than or equal to 10 wt %, greater than or equal to 12.5 wt %, greater than or equal to 15 wt %, greater than or equal to 20 wt %, greater than or equal to 25 wt %, greater than or equal to 30 wt %, greater than or equal to 35 wt %, greater than or equal to 40 wt %, greater than or equal to 50 wt %, greater than or equal to 60 wt %, greater than or equal to 75 wt %, greater than or equal to 90 wt %, greater than or equal to 95 wt %, greater than or equal to 97.5 wt %, greater than or equal to 99 wt %, greater than or equal to 99.5 wt %, greater than or equal to 99.9 wt %, or greater than or equal to 99.99 wt % of the carbon-based portion. Carbon may make up less than or equal to 100 wt %, less than or equal to 99.99 wt %, less than or equal to 99.9 wt %, less than or equal to 99.5 wt %, less than or equal to 99 wt %, less than or equal to 97.5 wt %, less than or equal to 95 wt %, less than or equal to 90 wt %, less than or equal to 75 wt %, less than or equal to 60 wt %, less than or equal to 50 wt %, less than or equal to 40 wt %, less than or equal to 35 wt %, less than or equal to 30 wt %, less than or equal to 25 wt %, less than or equal to 20 wt %, less than or equal to 15 wt %, or less than or equal to 12.5 wt % of the carbon-based portion. Combinations of the above-referenced ranges are also possible (e.g., greater than or equal to 10 wt % and less than or equal to 100 wt %, or greater than or equal to 30 wt % and less than or equal to 100 wt %). Other ranges are also possible.

Carbon-based portions described herein may have a variety of suitable geometries. In some embodiments, the carbon-based portion comprises a particle. Non-limiting examples of suitable types of particles include carbon black particles, particles comprising elemental carbon, and particles comprising graphite (e.g., highly-oriented pyrolytic graphite, pyrolytic graphite). In some embodiments, the carbon-based portion has a morphology comprising at least one dimension that is nanoscale (e.g., that extends for a length of less than or equal to 100 nm) and comprising at least one dimension that is not nanoscale (e.g., that extends for a length of greater than or equal to 100 nm). For instance, the carbon-based portion may comprise a two-dimensional material (i.e., a material comprising one nanoscale dimension and two dimensions that are not nanoscale) or may comprise a one-dimensional material (i.e., a material comprising two nanoscale dimension and one dimension that is not nanoscale). One example of a suitable two-dimensional material is graphene. One example of a suitable one-dimensional material is a carbon nanotube. When carbon nanotubes are employed, they may be single wall or multi wall.

In some embodiments, a carbon-based material comprises a carbon-based portion that comprises a graphene in the form of a plurality of graphene sheets, and the graphene sheets are spaced apart from each other to a relatively high degree. In some embodiments, the graphene sheets are spaced apart from each other such that the strength of the van der Waals interactions between the graphene sheets is substantially reduced in comparison to other forms of graphene. For instance, the strength of the van der Waals interactions between the graphene sheets may be less than or equal to 10%, less than or equal to 5%, less than or equal to 2%, or less than or equal to 1% of the strength of the van der Waals interactions between the graphene sheets in bulk graphite. In some embodiments, the strength of the van der Waals interactions between the graphene sheets is greater than or equal to 0%, greater than or equal to 1%, greater than or equal to 2%, or greater than or equal to 5% of the strength of the van der Waals interactions between the graphene sheets in bulk graphite. Combinations of the above-referenced ranges are also possible (e.g., less than or equal to 10% and greater than or equal to 0%). Other ranges are also possible.

In some embodiments, a carbon-based material comprises a carbon-based portion that comprises a graphene in the form of a plurality of graphene sheets and the graphene sheets are spaced apart from each other to a relatively uniform degree. For instance, in some embodiments, a relatively high percentage of the graphene sheets are spaced apart from their nearest neighbors by a distance of greater than or equal to 3 Å. In some embodiments, greater than or equal to 70%, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or greater than or equal to 99.99% of the graphene sheets are spaced apart from their nearest neighbors by a distance of greater than or equal to 3 Å. In some embodiments, less than or equal to 100%, less than or equal to 99.99%, less than or equal to 99.9%, less than or equal to 99.5%, less than or equal to 99%, less than or equal to 97.5%, less than or equal to 95%, less than or equal to 90%, less than or equal to 85%, less than or equal to 80%, or less than or equal to 75% of the graphene sheets are spaced apart from their nearest neighbors by a distance of greater than or equal to 3 Å. Combinations of the above-referenced ranges are also possible (e.g., greater than or equal to 70% and less than or equal to 100%). Other ranges are also possible.

In some embodiments, a relatively high percentage of the graphene sheets are spaced apart from their nearest neighbors by a distance of greater than or equal to 8 Å. In some embodiments, greater than or equal to 70%, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or greater than or equal to 99.99% of the graphene sheets are spaced apart from their nearest neighbors by a distance of greater than or equal to 8 Å. In some embodiments, less than or equal to 100%, less than or equal to 99.99%, less than or equal to 99.9%, less than or equal to 99.5%, less than or equal to 99%, less than or equal to 97.5%, less than or equal to 95%, less than or equal to 90%, less than or equal to 85%, less than or equal to 80%, or less than or equal to 75% of the graphene sheets are spaced apart from their nearest neighbors by a distance of greater than or equal to 8 Å. Combinations of the above-referenced ranges are also possible (e.g., greater than or equal to 70% and less than or equal to 100%). Other ranges are also possible.

In some embodiments, a relatively high percentage of the graphene sheets are spaced apart from their nearest neighbors by a distance of greater than or equal to 12 Å. In some embodiments, greater than or equal to 70%, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or greater than or equal to 99.99% of the graphene sheets are spaced apart from their nearest neighbors by a distance of greater than or equal to 12 Å. In some embodiments, less than or equal to 100%, less than or equal to 99.99%, less than or equal to 99.9%, less than or equal to 99.5%, less than or equal to 99%, less than or equal to 97.5%, less than or equal to 95%, less than or equal to 90%, less than or equal to 85%, less than or equal to 80%, or less than or equal to 75% of the graphene sheets are spaced apart from their nearest neighbors by a distance of greater than or equal to 12 Å. Combinations of the above-referenced ranges are also possible (e.g., greater than or equal to 70% and less than or equal to 100%). Other ranges are also possible.

In some embodiments, a relatively high percentage of the graphene sheets are spaced apart from their nearest neighbors by a distance of greater than or equal to 10 Å. In some embodiments, greater than or equal to 70%, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or greater than or equal to 99.99% of the graphene sheets are spaced apart from their nearest neighbors by a distance of greater than or equal to 10 Å. In some embodiments, less than or equal to 100%, less than or equal to 99.99%, less than or equal to 99.9%, less than or equal to 99.5%, less than or equal to 99%, less than or equal to 97.5%, less than or equal to 95%, less than or equal to 90%, less than or equal to 85%, less than or equal to 80%, or less than or equal to 75% of the graphene sheets are spaced apart from their nearest neighbors by a distance of greater than or equal to 10 Å. Combinations of the above-referenced ranges are also possible (e.g., greater than or equal to 70% and less than or equal to 100%). Other ranges are also possible.

In some embodiments, a relatively high percentage of the graphene sheets are spaced apart from their nearest neighbors by a distance of greater than or equal to 15 Å. In some embodiments, greater than or equal to 70%, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or greater than or equal to 99.99% of the graphene sheets are spaced apart from their nearest neighbors by a distance of greater than or equal to 15 Å. In some embodiments, less than or equal to 100%, less than or equal to 99.99%, less than or equal to 99.9%, less than or equal to 99.5%, less than or equal to 99%, less than or equal to 97.5%, less than or equal to 95%, less than or equal to 90%, less than or equal to 85%, less than or equal to 80%, or less than or equal to 75% of the graphene sheets are spaced apart from their nearest neighbors by a distance of greater than or equal to 15 Å. Combinations of the above-referenced ranges are also possible (e.g., greater than or equal to 70% and less than or equal to 100%). Other ranges are also possible.

When a carbon-based material comprises a carbon-based portion that comprises a graphene in the form of a plurality of graphene sheets, the graphene sheets may be spaced apart from each other such that a d-spacing may be observed by powder X-ray diffraction. The observed d-spacing may be greater than or equal to 2 Å, greater than or equal to 2.5 Å, greater than or equal to 3 Å, greater than or equal to 3.5 Å, greater than or equal to 4 Å, greater than or equal to 5 Å, greater than or equal to 5.5 Å, greater than or equal to 6 Å, greater than or equal to 6.5 Å, greater than or equal to 7 Å, greater than or equal to 7.5 Å, greater than or equal to 8 Å, greater than or equal to 8.5 Å, greater than or equal to 9 Å, greater than or equal to 9.5 Å, greater than or equal to 10 Å, greater than or equal to 10.5 Å, greater than or equal to 11 Å, greater than or equal to 11.5 Å, greater than or equal to 12 Å, greater than or equal to 12.5 Å, greater than or equal to 13 Å, greater than or equal to 13.5 Å, greater than or equal to 14 Å, greater than or equal to 14.5 Å, greater than or equal to 15 Å, or greater than or equal to 15.5 Å. The observed d-spacing may be less than or equal to 16 Å, less than or equal to 15.5 Å, less than or equal to 15 Å, less than or equal to 14.5 Å, less than or equal to 14 Å, less than or equal to 13.5 Å, less than or equal to 13 Å, less than or equal to 12.5 Å, less than or equal to 12 Å, less than or equal to 11.5 Å, less than or equal to 11 Å, less than or equal to 10.5 Å, less than or equal to 10 Å, less than or equal to 9.5 Å, less than or equal to 9 Å, less than or equal to 8.5 Å, less than or equal to 8 Å, less than or equal to 7.5 Å, less than or equal to 7 Å, less than or equal to 6.5 Å, less than or equal to 6 Å, less than or equal to 5.5 Å, less than or equal to 5 Å, less than or equal to 4.5 Å, less than or equal to 4 Å, less than or equal to 3.5 Å, less than or equal to 3 Å, or less than or equal to 2.5 Å. Combinations of the above-referenced ranges are also possible (e.g., greater than or equal to 2 Å and less than or equal to 16 Å, greater than or equal to 3 Å and less than or equal to 3.5 Å, greater than or equal to 8 Å and less than or equal to 8.5 Å, greater than or equal to 12.5 Å and less than or equal to 13 Å, or greater than or equal to 15 Å and less than or equal to 15.5 Å). Other ranges are also possible.

In some embodiments, a carbon-based material comprises a carbon-based portion that comprises a graphene in the form of a plurality of graphene sheets that are not uniformly spaced as evidenced by powder X-ray diffraction. For instance, a carbon-based material may have a powder X-ray diffraction pattern that does not show any peaks indicative of a spacing between the graphene sheets or may have a powder X-ray diffraction pattern that shows a broad peak indicative of a large range of spacings between the graphene sheets.

When a carbon-based material comprises a carbon-based portion that comprises a graphene in the form of a plurality of graphene sheets, the graphene sheets may be uniformly spaced. For instance, the graphene sheets may be spaced apart from their nearest neighbors such that each nearest neighbor spacing is within 50%, within 40%, within 30%, within 25%, within 20%, within 15%, within 12.5%, within 10%, within 7.5%, within 5%, within 4%, within 3%, within 2.5%, or within 1% of the average nearest neighbor spacing between graphene sheets. The average nearest neighbor spacing between graphene sheets may be determined by powder X-ray diffraction. One example of a carbon-based material comprising uniformly-spaced graphene sheets is Stage 1 GIC, described in Example 1 in more detail.

In other embodiments, a carbon-based material comprises a carbon-based portion that comprises a graphene in the form of a plurality of graphene sheets that are not uniformly spaced. For instance, the graphene sheets may be spaced apart from their nearest neighbors in a manner such that the nearest neighbor spacings fall outside of the ranges described above. Without wishing to be bound by any particular theory, it is believed that graphene sheets that are not uniformly spaced may be desirable for a number of reasons. As an example, a lack of uniform spacing between the graphene sheets may be indicative of graphene sheets that are spaced relatively far apart from each other and/or that graphene sheets between which the strength of the van der Waals interactions is substantially reduced. These graphene sheets may desirably be easily dispersed in a solvent. The graphene sheets may be dispersed in the solvent through application of mechanical energy, such as shear and/or sonication. In some embodiments, exposure of the graphene sheets to a species with which it is reactive, such as a species that forms covalent bonds with the graphene, may cause the graphene sheets to react with the species with which it is reactive. The reaction may cause the graphene sheets to spontaneously dissolve in the solvent. Such species may include electrophilic species, such as diazonium ions.

When a carbon-based material comprises a carbon-based portion that comprises a graphene in the form of a plurality of graphene sheets, one or more species may be intercalated between the graphene sheets. The species may be an ionic composition comprising one or more ions (associated with each other or dissociated from each other). The ionic composition may comprise an organic cation, such as an ammonium ion and/or a phosphonium ion. When present, the ammonium ion may be a quaternary ammonium ion, such as a tetrabutylammonium ion. The species intercalated between the graphene sheets, if present, may have a variety of suitable morphologies. In some embodiments, a species that is a decomposition product (e.g., an electrolytic decomposition product) of a species initially intercalated between the graphene sheets may be intercalated between the graphene sheets (e.g., in addition to, or instead of, the species initially intercalated).

Non-limiting examples of such species include decomposition products of the ions described above, such as amines (e.g., tributylamine), alkenes (e.g., butene), and/or alkanes. The species intercalated between the graphene sheets may be crystalline, amorphous, and/or partially crystalline and partially amorphous.

As described above, some embodiments comprise applying a voltage to a carbon-based material. The voltage may be a voltage that is constant for at least a period of time and/or may be a voltage that varies over time. The voltage, whether varying or constant, may have a value of greater than or equal to −3.15 V, greater than or equal to −3.1 V, greater than or equal to −3.05 V, greater than or equal to −3 V, greater than or equal to −2.95 V, greater than or equal to −2.9 V, greater than or equal to −2.85 V, greater than or equal to −2.8 V, greater than or equal to −2.75 V, greater than or equal to −2.7 V, greater than or equal to −2.65 V, greater than or equal to −2.6 V, greater than or equal to −2.55 V, greater than or equal to −2.5 V, greater than or equal to −2.45 V, greater than or equal to −2.4 V, greater than or equal to −2.35 V, greater than or equal to −2.3 V, or greater than or equal to −2.25 V at at least one point in time. In some embodiments, a method comprises applying a voltage, varying or constant, to the carbon-based material of less than or equal to −2.2 V, less than or equal to −2.25 V, less than or equal to −2.3 V, less than or equal to −2.35 V, less than or equal to −2.4 V, less than or equal to −2.45 V, less than or equal to −2.5 V, less than or equal to −2.55 V, less than or equal to −2.6 V, less than or equal to −2.65 V, less than or equal to −2.7 V, less than or equal to −2.75 V, less than or equal to −2.8 V, less than or equal to −2.85 V, less than or equal to −2.9 V, less than or equal to −2.95 V, less than or equal to −3 V, less than or equal to −3.05 V, or less than or equal to −3.1 V at at least one point in time. Combinations of the above-referenced ranges are also possible (e.g., greater than or equal to −3.15 V and less than or equal to −2.2 V). Other ranges are also possible.

Voltage applied to a carbon-based material that varies over time may do so in a variety of suitable ways. For instance, a voltage may be applied to a carbon-based material that increases or decreases (e.g., linearly) over time. In such cases, the starting voltage, the final voltage, and/or all of the voltages applied may be in one or more of the ranges described in the previous paragraph. In some embodiments, the voltage varies relatively slowly over time. For instance, the voltage may increase or decrease at a rate of greater than or equal to 2 µV/s, greater than or equal to 5 µV/s, greater than or equal to 10 µV/s, greater than or equal to 15 µV/s, greater than or equal to 20 µV/s, greater than or equal to 25 µV/s, greater than or equal to 30 µV/s, or greater than or equal to 35 µV/s. In some embodiments, the voltage increases or decreases at a rate of less than or equal to 40 µV/s, less than or equal to 35 µV/s, less than or equal to 30 µV/s, less than or equal to 25 µV/s, less than or equal to 20 µV/s, less than or equal to 15 µV/s, less than or equal to 10 µV/s, or less than or equal to 5 µV/s. Combinations of the above-referenced ranges are also possible (e.g., greater than or equal to 2 µV/s and less than or equal to 40 µV/s). Other ranges are also possible.

In some embodiments, a voltage is applied to a carbon-based material in the presence of a solvent and/or a combination of solvents. One or more species may be dissolved in the solvent and/or combination of solvents, and may intercalate into the carbon-based material upon application of the voltage thereto. Application of the voltage to the carbon-based material may cause this intercalation to occur. Suitable solvents may be those that can dissolve the species intercalating into the carbon-based material in appreciable amounts (e.g., in amounts that promote a desirable amount of intercalation of the species into the carbon-based material) and/or that promote intercalation of the species into the carbon-based material.

By way of example, in some embodiments, a combination of solvents comprises a solvent with a wide electrochemical window and a solvent having a similar surface tension to the carbon-based material (e.g., a surface tension similar to graphene and/or graphite). The solvent with the wide electrochemical window may be stable to oxidation and reduction at a wide variety of voltages, such as the voltage or voltages applied to the carbon-based material during intercalation of the species therein. It may dissolve the species to be intercalated during the intercalation process. The solvent that has a similar surface tension to the carbon-based material may promote wetting of the carbon-based material by the solvent, thus placing the species dissolved therein in close proximity to the carbon-based material and promoting intercalation of the species into the carbon-based material. One example of a particularly advantageous combination of solvents is a combination of solvents comprising acetonitrile and dimethylformamide.

When a voltage is applied to a carbon-based material in the presence of a solvent with a wide electrochemical window, the solvent with a wide electrochemical window may be stable at a voltage of greater than or equal to −3.15 V, greater than or equal to −3.1 V, greater than or equal to −3.05 V, greater than or equal to −3 V, greater than or equal to −2.95 V, greater than or equal to −2.9 V, greater than or equal to −2.85 V, greater than or equal to −2.8 V, greater than or equal to −2.75 V, greater than or equal to −2.7 V, greater than or equal to −2.65 V, greater than or equal to −2.6 V, greater than or equal to −2.55 V, greater than or equal to −2.5 V, greater than or equal to −2.45 V, greater than or equal to −2.4 V, greater than or equal to −2.35 V, greater than or equal to −2.3 V, or greater than or equal to −2.25 V. In some embodiments, the solvent with a wide electrochemical window may be stable at a voltage of less than or equal to −2.2 V, less than or equal to −2.25 V, less than or equal to −2.3 V, less than or equal to −2.35 V, less than or equal to −2.4 V, less than or equal to −2.45 V, less than or equal to −2.5 V, less than or equal to −2.55 V, less than or equal to −2.6 V, less than or equal to −2.65 V, less than or equal to −2.7 V, less than or equal to −2.75 V, less than or equal to −2.8 V, less than or equal to −2.85 V, less than or equal to −2.9 V, less than or equal to −2.95 V, less than or equal to −−3 V, less than or equal to −3.05 V, or less than or equal to −3.1 V. Combinations of the above-referenced ranges are also possible (e.g., greater than or equal to −3.15 V and less than or equal to −2.2 V). Other ranges are also possible. In some embodiments, a solvent with a wide electrochemical window may be stable throughout one or more of the ranges listed above (e.g., stable at all voltages of greater than or equal to −3.15 V and less than or equal to −2.2 V). One example of a suitable solvent with a high electrochemical window is acetonitrile.

In some embodiments, a voltage is applied to a carbon-based material in the presence of a solvent that is unstable at that voltage (e.g., in addition to a solvent that is stable at the voltage applied to the carbon-based material). The unstable solvent may at least partially decompose when the voltage is applied to the carbon-based material. In other words, the voltage applied to the carbon-based material may cause at least a portion of a solvent to which the carbon-based material is exposed to at least partially decompose. By way of example, in some embodiments, a voltage is applied to a carbon-based material in the presence of a solvent that is unstable at a voltage in one or more of the ranges described above (e.g., at a voltage of greater than or equal to −3.15 V and less than or equal to −2.2 V).

When a solvent has a similar surface tension to that of the carbon-based material, the surface tension of the solvent may be within 25%, within 20%, within 15%, within 10%, within 5%, within 2%, or within 1% of the surface tension of the carbon-based material. In some embodiments, a solvent with a similar surface tension to that of the carbon-based material has a surface tension of greater than or equal to 30 mN/m, greater than or equal to 32 mN/m, greater than or equal to 34 mN/m, greater than or equal to 36 mN/m, greater than or equal to 38 mN/m, greater than or equal to 40 mN/m, greater than or equal to 42 mN/m, greater than or equal to 44 mN/m, or greater than or equal to 48 mN/m. In some embodiments, a solvent with a similar surface tension to that of the carbon-based material has a surface tension of less than or equal to 50 mN/m, less than or equal to 48 mN/m, less than or equal to 46 mN/m, less than or equal to 44 mN/m, less than or equal to 42 mN/m, less than or equal to 40 mN/m, less than or equal to 38 mN/m, less than or equal to 36 mN/m, less than or equal to 34 mN/m, or less than or equal to 32 mN/m. Combinations of the above-referenced ranges are also possible (e.g., greater than or equal to 30 mN/m and less than or equal to 50 mN/m). Other ranges are also possible.

In some embodiments, a solvent with a similar surface tension to a carbon-based material is polar and/or aprotic. Non-limiting examples of suitable solvents with surface tensions similar to the surface tensions of some carbon-based materials include N-methyl-2-pyrrolidone, dimethylformamide, and propylene carbonate.

A variety of suitable species may be dissolved in a solvent to which a carbon-based material is exposed. In some embodiments, the species is not reactive with (and/or does not react with) the carbon-based material during and/or after the intercalation process. The species may decompose, at least partially, after intercalation. For instance, in some embodiments, tetrabutylammonium ions intercalate into a carbon-based material such as graphene, and then decompose into other species (e.g., amines such as tributylamine, alkenes such as butene, one or more alkanes) after intercalation. The decomposition may be caused by an electrolytic reaction. In some embodiments, the species is one or more of the species described above that may be intercalated into a carbon-based material and/or between graphene sheets in a carbon-based material.

When a voltage is applied to a carbon-based material, the carbon-based material may be supplied in a variety of suitable forms. In some embodiments, the carbon-based material is in powder form.

For convenience, certain terms employed in the specification, examples, and appended claims are listed here. Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R'") wherein R', R", and R'" each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

EXAMPLE 1

Abstract

This Example describes the covalent modification of the 7c-electron basal planes of graphene, which may enable the formation of new materials with enhanced functionality. An electrochemical method for the formation of what is referred to herein as a Hyperstage-1 graphite intercalation compound (GIC) is described. The Hyperstage-1 GIC may have a large interlayer spacing $d_{001}$, such as $d_{001} > 15.3$ Å, and/or may contain disordered interstitial molecules and/or ions. The Hyperstage-1 GIC may be highly activated and/or may undergo spontaneous exfoliation when reacted with diazonium ions to produce soluble graphenes with relatively high functionalization densities. For instance, some Hyperstage-1 GIC may undergo spontaneous exfoliation when reacted with diazonium ions to produce a soluble graphene with one pendant aromatic ring for every 12 graphene carbons. It is believed that the Hyperstage-1 GIC state assists with forming soluble graphene of this type, as it is believed that this state exhibits weakened van der Waals coupling between adjacent graphene layers and/or that reactants have an enhanced ability to diffuse into the disordered intercalate phase between the layers. Graphene functionalization with 3,5-dinitrophenyl (3,5-DiNP) groups may result in high dispersibility (e.g., on the order of 0.24 mg ml$^{-1}$) in N,N-dimethylformamide (DMF) and/or may promote conjugation with amines.

Main

In this Example, a gentle room temperature (RT) method for reducing the van der Waals coupling between graphene sheets ($d_{001} > 15.3$ Å) and subsequent spontaneous exfoliation to give soluble functionalized graphene is described. This method may result in the production of pure isolated graphene sheets. In some embodiments, the pure isolated graphene sheets may be produced quantiatively and/or in a manner that can be separated from any multilayer graphene sheets also produced. The method described in this Example comprises the intercalation of tetrabutylammonium (TBA$^+$) into the graphene galleries. The TBA$^+$ may electrostatically balance the negatively charged π-electron system created electrochemically. Increased $d_{001}$-spacing in Stage-1 GIC may reduce van der Waals interactions between graphenes. However, as described further below, the crystalline organization of the TBA$^+$ ions, may restrict reactant diffusion into the network, which may reduce reactivity. At high negative potentials, it may be possible to increase the intercalation of large density of TBA$^+$ ions and/or to introduce amines by electrolytic decomposition of the TBA$^+$. These processes may result in the formation of a further expanded gallery with a disordered interstitial phase between the basal planes to give what is referred to herein as a Hyperstage-1 GIC. The resultant material may be desirable because it may have a morphology such that every graphene layer (or a large portion of the graphene layers) is accessible to react with diazonium salts. Reaction with the diaozonium salts may cause the graphene to spontaneously exfoliate and/or to exfoliate without any deliberate mixing or sonication. The diazonium reaction of the Hyperstage-1 GIC may result in desirably high densities of functional groups on the graphene. Functionalization with 3,5-dinitrophenyl may also enable the formation of Meisenheimer complexes between functionalized graphene and n-butylamine.

Figure 9:
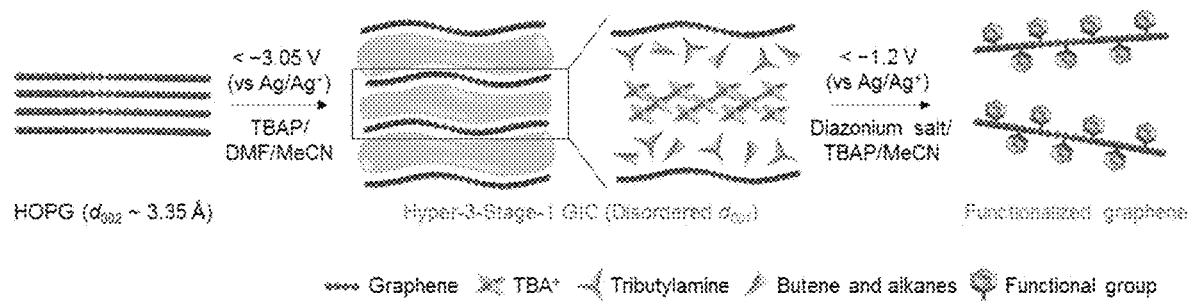
FIGS. 9-10 are schematic depictions of methods of intercalating a species into a carbon-based material, in accordance with some embodiments.

It may be desirable to create extended functionalized graphenes with minimal defects in the hexagonal graphene lattice. For this Example, highly oriented pyrolytic graphite (HOPG) was employed as a high purity graphite source. HOPG may advantageously conserve its monolithic structure and conserve the electrical connectivity of the graphite domains throughout the expansion that accompanies the electrochemical generation of the different GICs. The electrochemically driven intercalation process is depicted in FIG. 9. In this scheme, applying a high reducing potential to HOPG results in TBA intercalation between the graphene sheets. The solvent employed may affect this process, and it is found that a mixture of acetonitrile (MeCN) and dimethylformamide (DMF) may enhance this process. A continuous electrochemical potential ramp may be employed to maintain a driving force for full intercalation of TBA$^+$, which may be accompanied by a dramatic volumetric expansion of HOPG.

Figure 10:
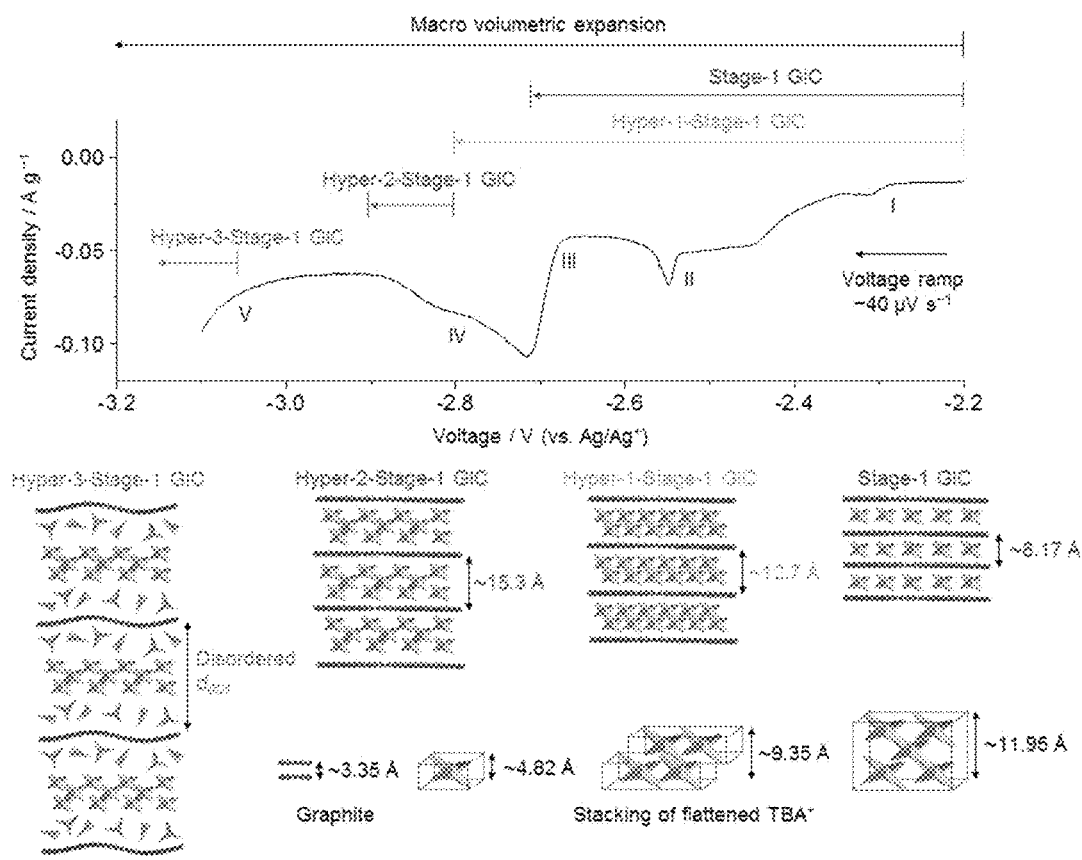
Figure 11:
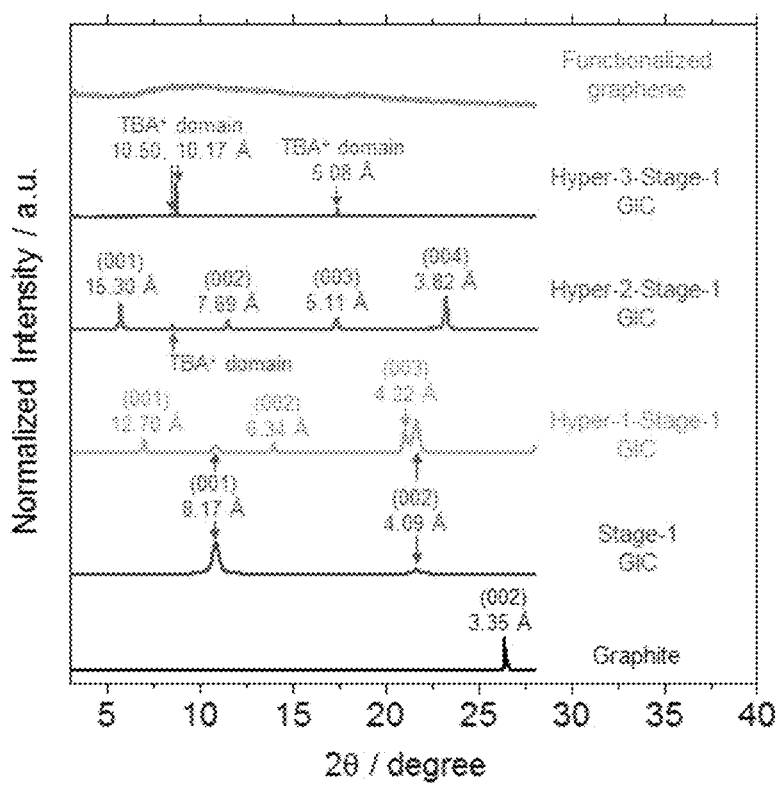
FIG. 11 is a plot showing X-ray diffraction data from carbon-based materials, in accordance with some embodiments.

In this process five voltage ranges were identified (I, II, III, IV and V in FIG. 10) that correspond to distinct phases of GIC staging. These include the Stage-1, Hyper-1-Stage-1, Hyper-2-Stage-1, and Hyper-3-Stage-1, which, as shown in FIG. 10, have varying degrees of ion intercalation and intersheet spacing. Since the electromigration of the larger molecule TBA$^+$ in graphene galleries was observed to be sluggish, specific current peaks associated with changes in staging were observed with extremely slow voltage sweeps (~40 μV s$^{-1}$). The different GIC stages were identified by X-ray diffraction (XRD), which reveals different crystallographic lattice arrangements of intercalants and graphite layers along the c-axis (FIG. 11). As intercalation took place, the graphite (002) peak vanished and new peaks appeared.

Figure 12:
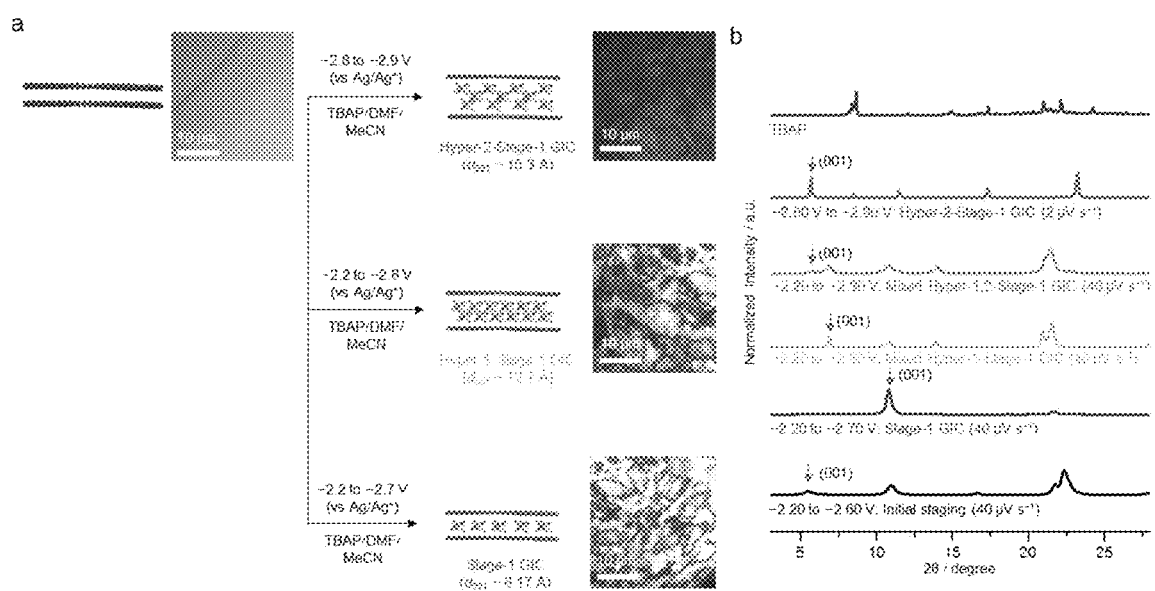
FIG. 12 shows a micrograph of a carbon-based material, a schematic depiction of a method of intercalating a species into a carbon-based material, and X-ray diffraction data from carbon-based materials, in accordance with some embodiments.
Figure 13:
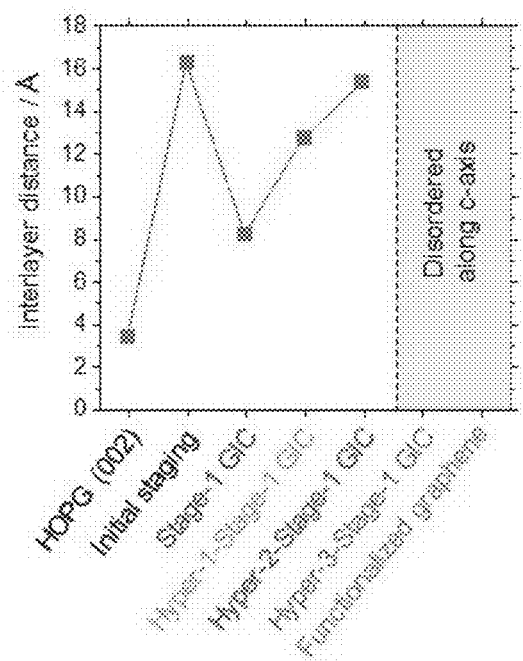
FIG. 13 is a plot showing the d-spacing for several carbon-based materials, in accordance with some embodiments.
Figure 14:
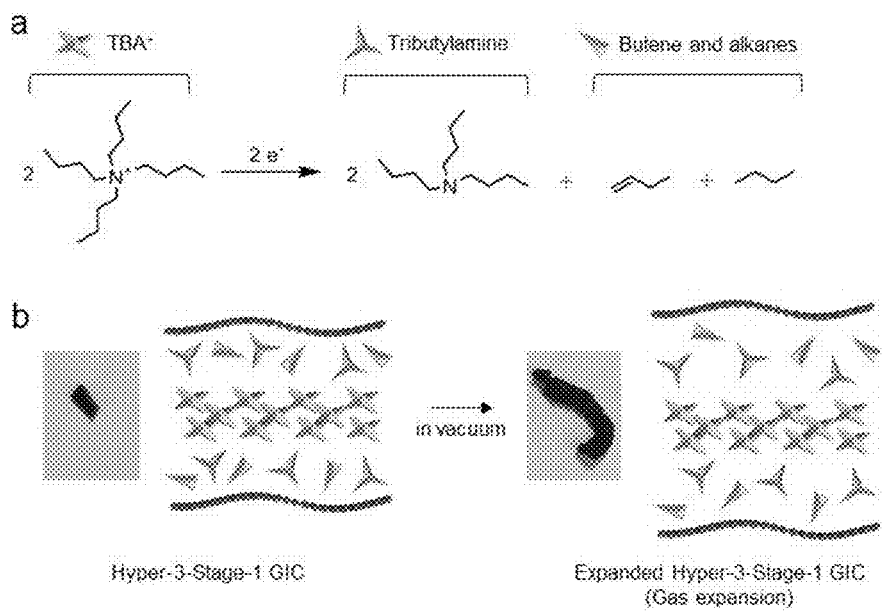
FIG. 14 is a schematic depiction of a method of intercalating a species into a carbon-based material, in accordance with some embodiments.
Figure 15:
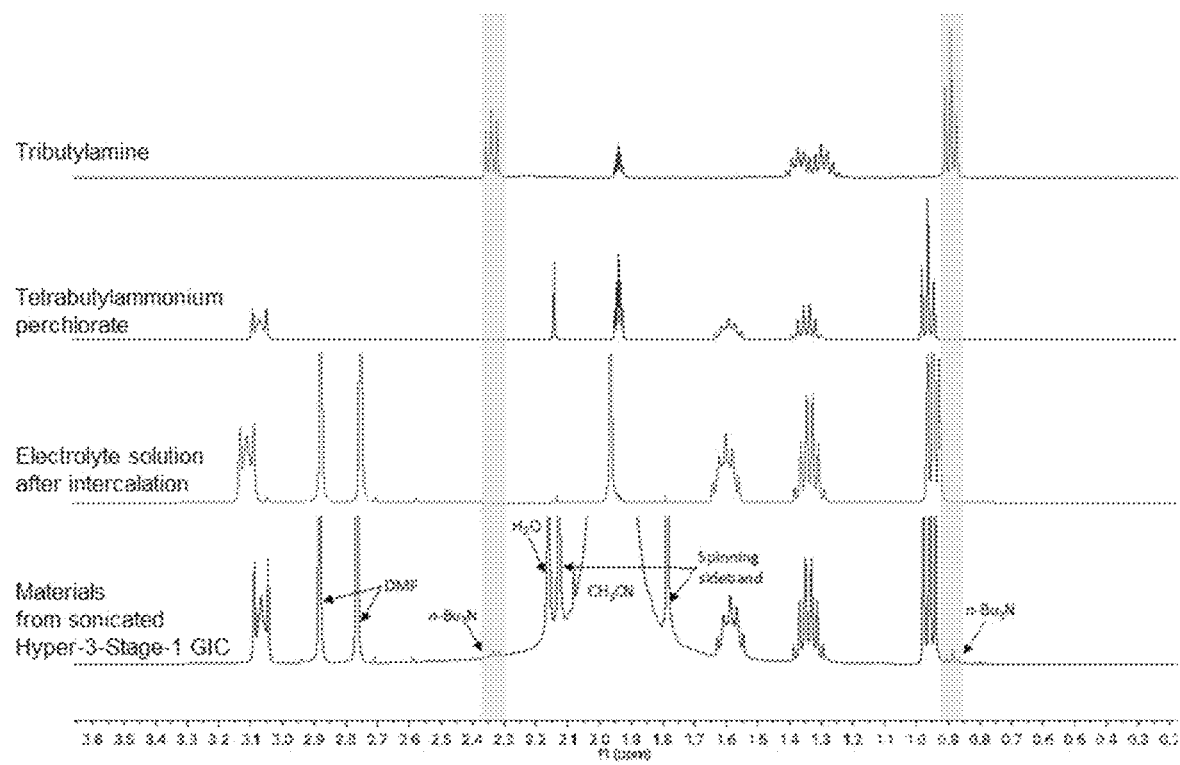
FIG. 15 is a plot showing NMR data from several carbon-based materials, in accordance with some embodiments.

The dominant diffractions in Stage-1 GIC that appeared in the (00 ℓ) reflections are a direct measure of the interlayer distance ($d_{001}$ of ~8.17 Å). The introduction of the intercalated layer weakened the attractive potential between graphite layers; however the material was still relatively inert as result of the ordered intercalation ions. The interlayer distance was in agreement with the expected size of TBA$^+$ in a flattened conformation (~-4.8 Å) within the graphene galleries. With increasing voltage, the graphene/TBA$^+$ matrix exhibited an increasing $d_{001}$ spacing (3.35→8.17→12.70→15.30 Å→disordered) (FIGS. 12 and 13). The structural disorder of the intercalation phase was highest for Hyper-3-Stage-1 GIC, which may be attributed to the reductive decomposition of TBA$^+$ ions within graphene galleries. Without wishing to be bound by any particular theory, it is believed that reductive fragmentation of TBA$^+$ ions caused decomposition of the TBA$^+$ ions into tributylamine, butene and alkanes (FIGS. 14 and 15). It is believed that these fragments disrupt much of the crystalline organization of the ions, which may facilitate functionalization. However, minor diffraction peaks were still observed. It is believed that these are due to the electrolyte.

Figure 16:
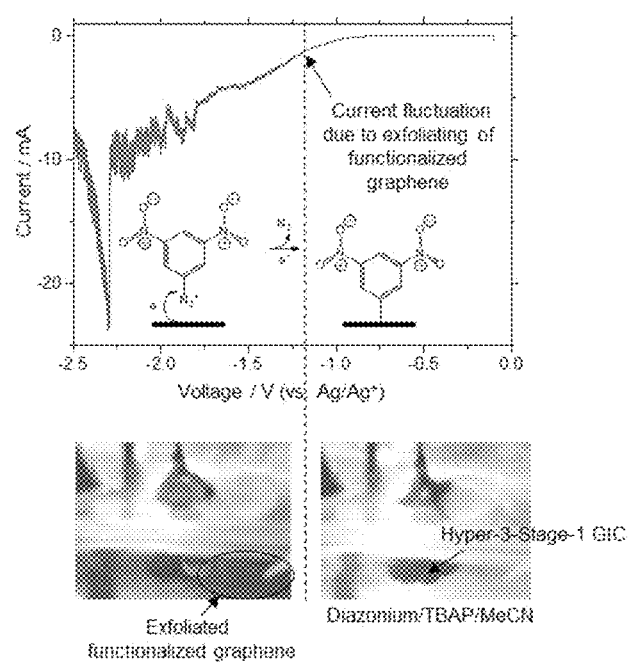
FIG. 16 shows current as a function of voltage for a carbon-based material and photographs of some carbon-based materials, in accordance with some embodiments.

The disorder in the Hyper-3-Stage-1 GIC produces was observed to enhance its reactivity, and transferring this material as an activated electrode to a solution containing 0.1 M 3,5-dinitrobenzenediazonium tetrafluoroborate (3,5-DiNBD) and 1 M TBAP in MeCN with a negative potential ramp from −1.2 to −2.0 V (vs. Ag/Ag$^+$, 10 µV S$^{-1}$) resulted in efficient reductive functionalization (FIG. 16). Under these conditions, the graphite was observed to undergo spontaneous exfoliation to give MeCN solutions of soluble functionalized graphene. XRD of the purified functionalized graphene revealed a completely amorphous material that lacks typical intergraphene sheet diffractions (FIG. 11). It is believed that this may be unusual for a functionalized graphene. It is believed that this behavior may be attributed this to the high degrees of functionalization, which may tend to prevent the sheets from organizing into 2D structures.

Figure 17:
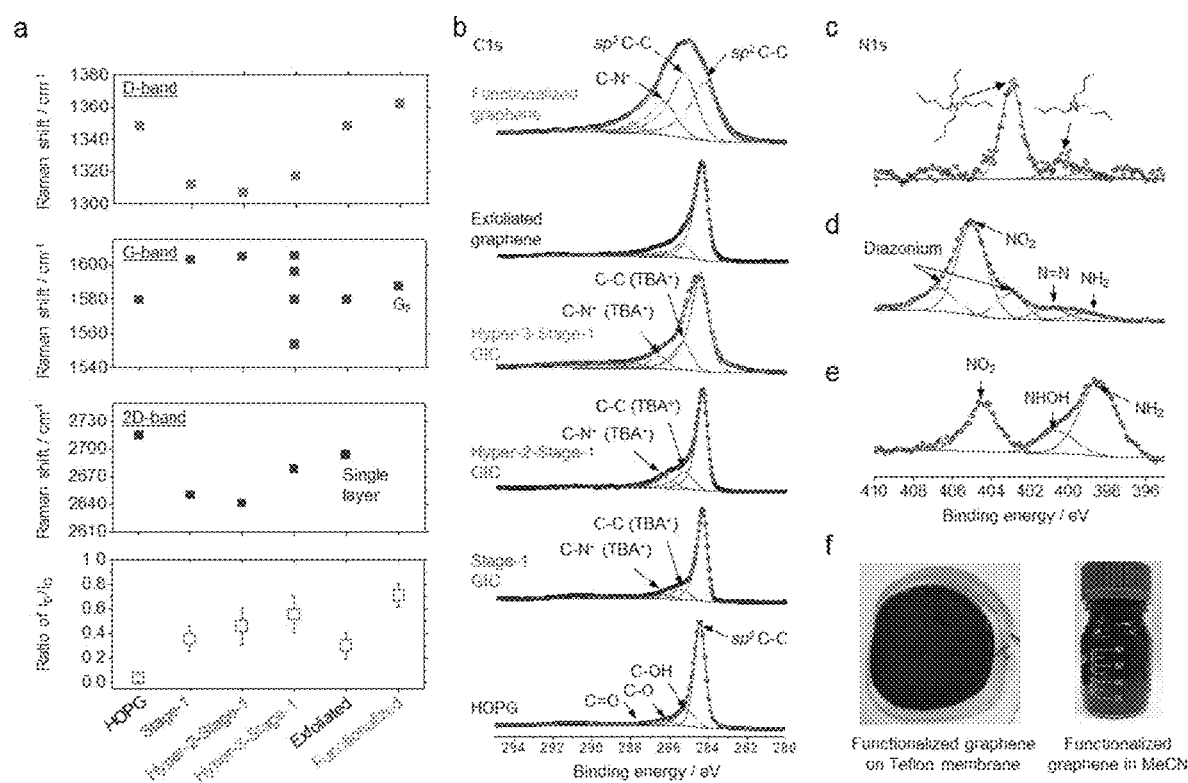
FIG. 17 shows data from some carbon-based materials, in accordance with some embodiments.
Figure 18:
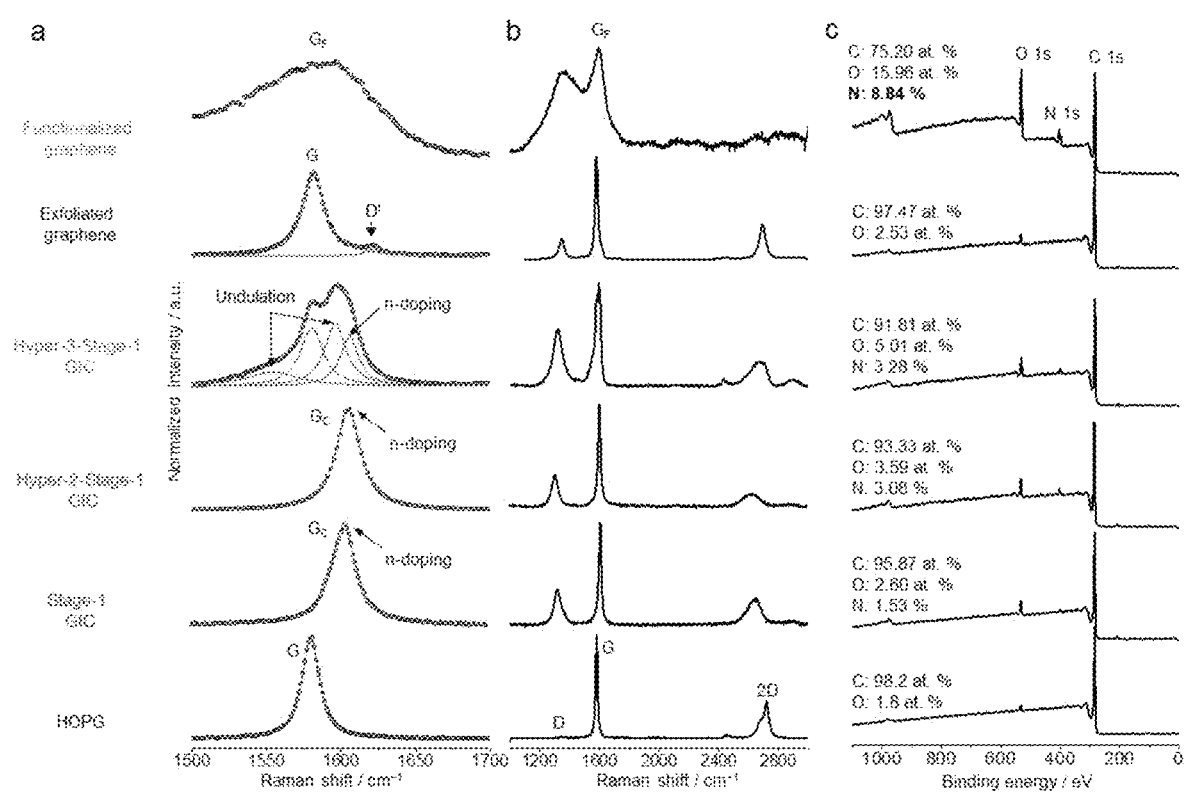
FIGS. 18-20 show Raman data from some carbon-based materials, in accordance with some embodiments.
Figure 19:
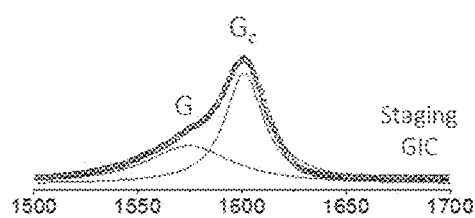

Raman spectroscopy was used to characterize HOPG, Stage-1, Hyper-2-Stage-1, Hyper-3-Stage-1 GICs, exfoliated graphene and functionalized graphene (FIG. 17A). The D and 2D-bands displayed similar shifts with TBA$^+$ intercalation and, in transition from HOPG to Hyper-2-Stage-1 GICs, these peaks gradually shifted to lower frequencies (−41.1 cm$^{-1}$ for D-band and −74.1 cm$^{-1}$ for 2D band). It is believed that these shifts are indicative of n-doping resulting from electrochemical reduction of the graphene with concurrent TBA$^+$ intercalation (FIG. 18). The D and 2D-bands broadened with increasing TBA$^+$ density, and the G-band split and shifted upon formation of different staged compounds (FIGS. 18 and 19). The G-band, which depends strongly on the charge carrier densities, and was observed to shift to higher frequencies. The G-band of graphite appeared at 1580 cm$^{-1}$ in HOPG and shifted to 1603.0-1605.1 cm$^{-1}$ in Stage-1/Hyper-2-Stage-1-GICs, respectively (FIGS. 17A and 18). The G band of Hyper-3-Stage-1 GIC also exhibited complexity, with multiple overlapped peaks that can be deconvoluted into 4 distinct peaks (FIGS. 17A and 18). It is believed that these peaks for Hyper-3-Stage-1 GIC can be assigned to n-doping with TBA$^+$ intercalation and to highly undulated graphene layers.

Figure 20:
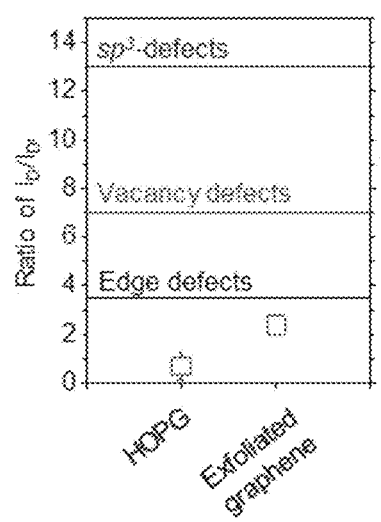
Figure 21:
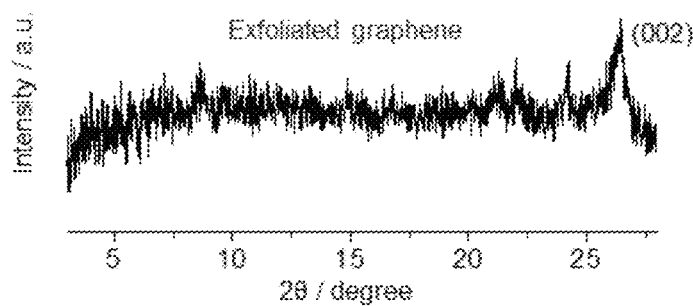
FIG. 21 shows X-ray diffraction data from a carbon-based material, in accordance with some embodiments.

The exfoliated (by ultrasonication) and purified (by washing) material was further analyzed. This analysis indicated that it is likely that electrochemical intercalation does not cause covalent functionalization of the graphene sheets. Specifically, the observed intensities of the Raman $I_D/I_G$ and $I_D/I_{D'}$ bands of exfoliated graphene from Hyper-3-Stage-1 GIC were 0.3 and 2.4, respectively (FIGS. 17A and 20). These exfoliated, defect free graphenes readily reassemble into stacked sheets when isolated, and the powders displayed the characteristic (002) reflection of graphite (FIG. 21). As a result, it is believed that the electrochemical activation did not result in irreversible functionalization of the graphene sheets. In contrast, after spontaneous exfoliation of functionalized graphene with 3,5-DiNP groups from Hyper-3-Stage-1 GIC, the Raman spectra indicated extensive covalent functionalization on the basal plane. The broadened lines of the D and G bands and the $I_D/I_G$ ratio (~0.71) suggest the introduction of a high percentage of sp$^3$-hybridized carbon atoms into the sp$^2$-hybridized graphene (FIGS. 17 and 18).

Figure 22:
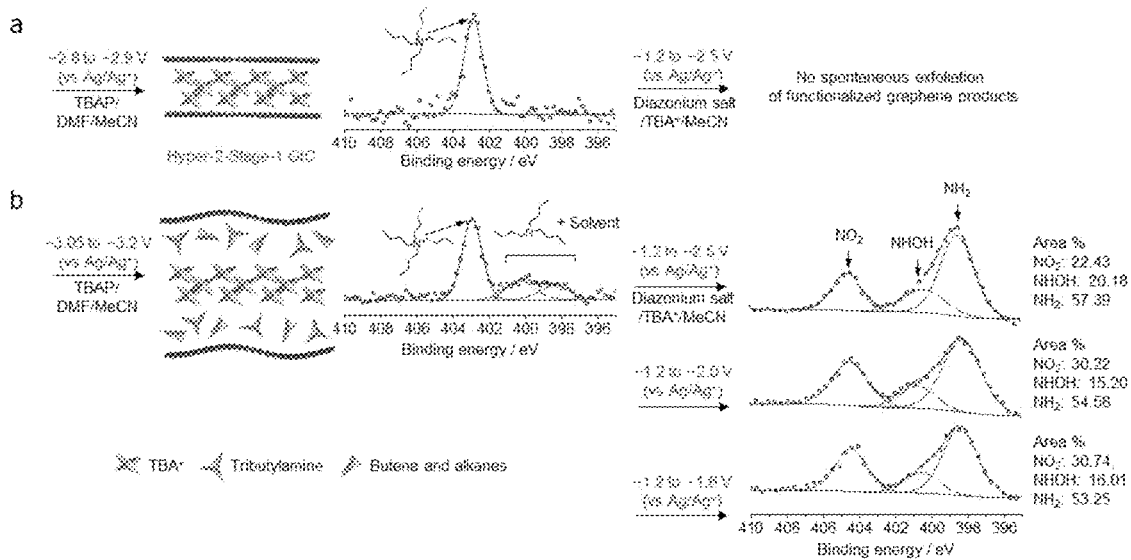
FIG. 22 shows a schematic depiction of a method of intercalating a species into a carbon-based material and X-ray photoelectric spectroscopy data from some carbon-based materials, in accordance with some embodiments.

XPS provides additional insight into the chemical nature of the GICs and functionalized graphene. The deconvolution of the C 1s peak revealed the presence of sp$^2$ C—C (~284.5 eV), sp$^3$ C—C/C—OH (~285.5 eV), C—O/C—N$^+$ (~286.3 eV), C=O (287.6 eV), and a shake-up peak (~291 eV) in FIG. 17B. The relative intensity of the different sp$^3$ component peaks (~285.5 and ~286.3 eV) in Stage-1, Hyper-2-Stage-1, Hyper-3-Stage-1 GICs were all consistent with the amount of intercalated TBA$^+$. The analysis of the nitrogen peaks is also relevant, and Hyper-2-Stage-1 and Hyper-3-Stage-1 GICs provided a pure intercalated phase with a peak at 402.8 eV corresponding to the N 1s of the quaternary TBA$^+$ (FIG. 22). The additional N 1s peaks at 400.3 eV and 398.4 eV in Hyper-3-Stage-1 GIC may be attributed to TBA$^+$ reduction products and solvent molecules (MeCN and DMF) in the graphene galleries (FIGS. 17C and 22).

Figure 23:
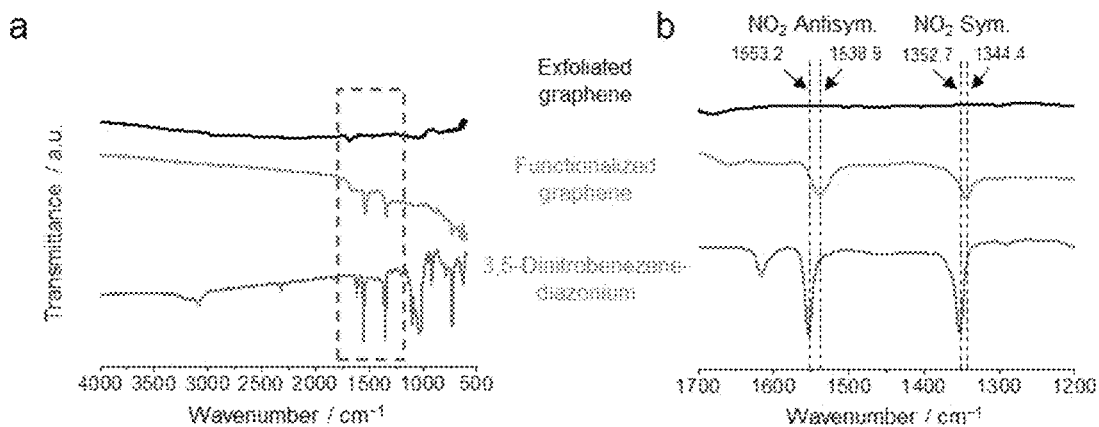
FIG. 23 shows ATR-FTIR data from some carbon-based materials, according to some embodiments.

XPS of graphene functionalized with 3,5-dinitrophenyl (3,5-DiNP) after purification produced a strong N is peak in the XPS spectra. The C/N ratio of ~8.5 reveals a high functionalization density of one 3,5-DiNP group per 12 carbon atoms (FIG. 18C). A high-resolution N 1s analysis revealed three peaks centered at 398.5, 400.5 and 404.7 eV (FIGS. 17D and 17E). The major peak at higher binding energy (404.7 eV) may be assigned to the nitrogen of the nitro groups, which suggests the presence of 3,5-DiNP groups attached to the graphene (FIGS. 22 and 23). The broad and lower binding energy N 1s peaks at 400.5 and 398.5 eV may be assigned to nitrogens from reduction of the nitro groups produced under the electrochemical conditions. Specifically, and without wishing to be bound by any particular theory, it is expected that reduction of the nitro groups will give rise to Ph-NHOH and/or Ph-NH$_2$ units. These processes may also be facilitated by the H atoms that can be extracted from the solvent and/or from the products generated by the reductive decomposition of the TBA$^+$ electrolyte. The XRD data and the peaks associated with ordered TBA$^+$ ions suggest that ordered TBA$^+$ ions in the gallery provide for a rigid network that blocks diffusion of other reagents into the interior of the material. The introduction of amine reduction products in Hyper-3-Stage-1, evidenced by the XPS N 1s peaks, produced disorder in the graphene galleries which may have allowed diazonium reagents to diffuse into the galleries (FIG. 10F).

Figure 24:
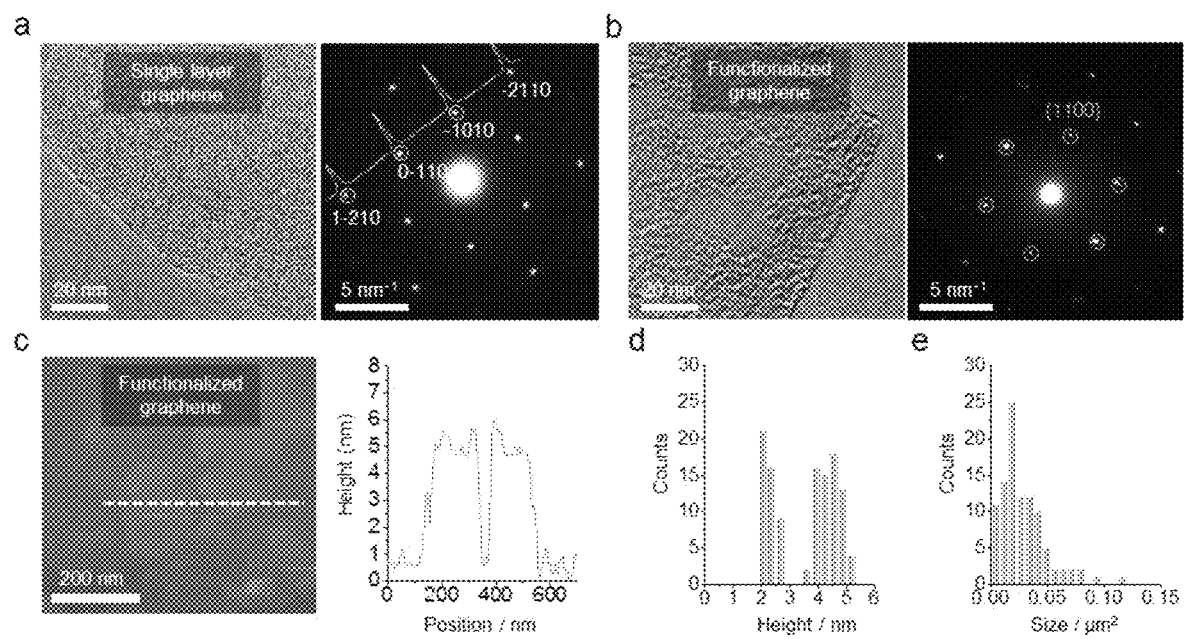
FIG. 24 shows micrographs of some carbon-based materials, according to some embodiments.
Figure 25:
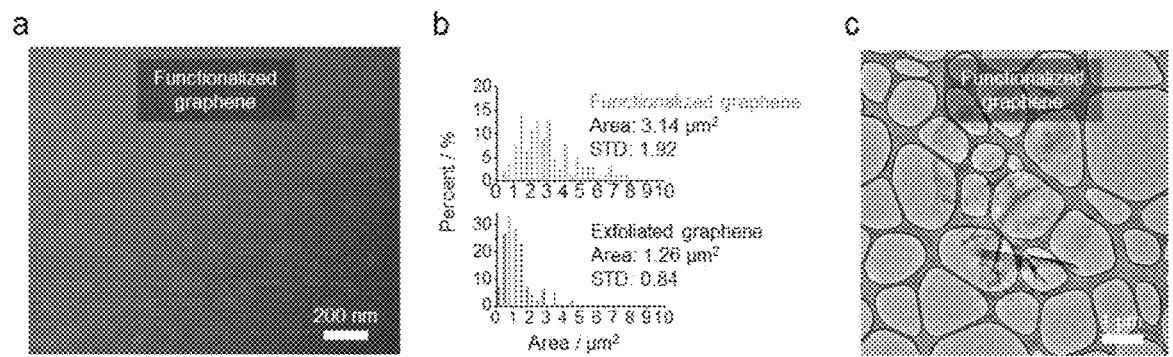
FIG. 25 shows an AFM micrograph, a TEM micrograph, and data generated by analyzing TEM micrographs of some carbon-based materials, according to some embodiments.

The functionalized graphene sheets were investigated by transmission electron microscopy (TEM) and atomic force microscopy (AFM) in order to obtain additional microscopic evidence of covalent functionalization. Exfoliated single layer graphene produced by ultrasonic exfoliation of the Hyper-3-Stage 1 GIC exhibited a single set of sharp peaks associated with a graphitic hexagonal diffraction pattern (FIG. 24A). The relative intensity ratio of $I_{\{1100\}}/I_{\{2110\}}$ was approximately 1.35. The surface of the graphene sheets appeared to have some heterogeneity, suggesting that some sections may be (possibly heavily) covered with pendant phenyl groups (FIG. 24B) and that other sections may have lower functionalization. In spite of the functionalization, the sample still displayed hexagonal crystalline domains. However, these domains were distorted, with a $d_{\{1100\}}$=2.12~2.28 Å as compared to graphene with $d_{\{1100\}}$=2.13 Å as determined by electron diffraction. An average thickness of ~4.3 nm was observed for functionalized graphenes according to the AFM profile (FIG. 24C). FIG. 24D shows a histogram of thickness of functionalized graphene, and reveals two distinct thicknesses of 2.4 and 4.4 nm. These heights are believed to correspond to two-sided functionalized single and double layer graphene structures, respectively, and suggest that the method described in this Example produces dominantly single/double layer exfoliations. The double layer structures may result from post functionalization aggregation. AFM analysis provided an average sheet area of 0.032 µm², which is smaller than the average domain size of the precursor graphite (intraplanar microcrystallic size: 1-10 µm) (FIGS. 24E and 25).

Figure 26:
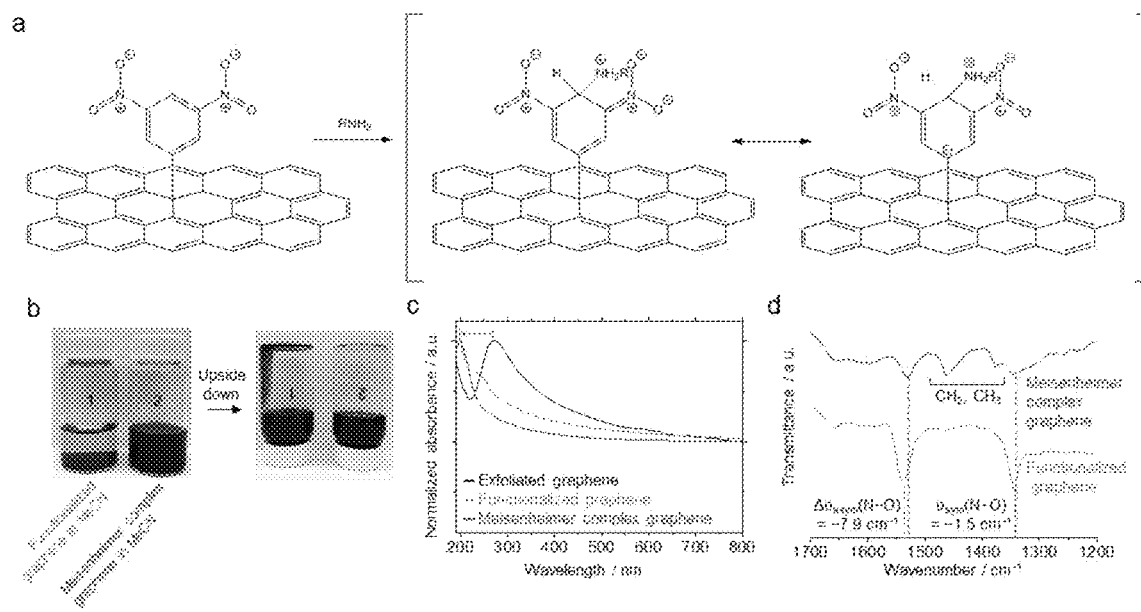
FIG. 26 shows a schematic depiction of a Meisenheimer complex, photographs of some carbon-based materials, and UV-vis and ATR-FTIR data from some carbon-based materials, in accordance with some embodiments.

Further experiments were performed to explore the ability of the electron-deficient 3,5-DiNP groups in the functionalized graphene described above to form Meisenheimer complexes with n-butylamine. A schematic illustration of Meisenheimer complex formation from 3,5-dintrobenzene functionalized graphene and n-butylamine is shown in FIG. 26A. When compared with the functionalized graphene with 3,5-DiNP groups, the Meisenheimer complex graphene had improved dispersion stability in MeCN (FIG. 26B). It was observed that graphene dispersed with n-butylamine did not form a stable dispersion and that the attachment of this molecule via a Meisenheimer complex increased the graphene's dispersibility in MeCN to give indefinitely stable solutions at concentrations of 0.9 mg mL⁻¹. The UV-Vis absorption spectra of exfoliated graphene, functionalized graphene, and Meisenheimer complex graphene dispersions in MeCN (FIG. 26C) support the proposed structures. The characteristic feature at 270 nm is believed to correspond to a $\pi$-$\pi$* plasmon peak where van Hove singularities occur. For the functionalized graphene, this peak blue-shifted to ~195.5 nm, suggesting that the electronic conjugation within the graphene was severely restricted by the sp³ defects.

Figure 27:
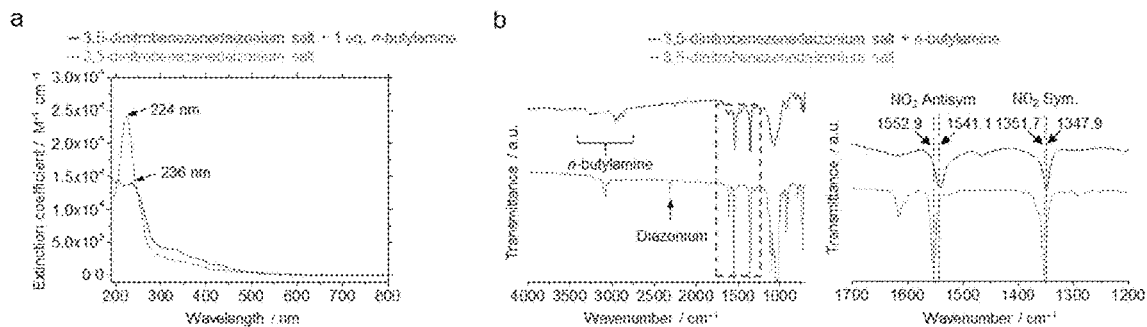
FIG. 27 shows UV-vis and ATR-FTIR data from some carbon-based materials, in accordance with some embodiments.

After functionalization, a new absorbance peak associated with the 3,5-DiNP group appeared at 249.1 nm (FIGS. 26C and 27). The strongly electron-withdrawing nitro groups in 3,5-dinitrobenzene favor Meisenheimer complexes with primary amines. This chemical characteristic was preserved in 3,5-DiNP functionalized graphene and FIG. 26A illustrates the formation of Meisenheimer complex with n-butylamine. The Meisenheimer complex graphene produced only small variations in the optical spectra (FIG. 26C), however, the complex is also evidenced by a weakening of the $NO_2$ infrared bands with a −7.9 cm⁻¹ shift on $\upsilon_{asym}$(N—O) and −1.5 cm⁻¹ on $\upsilon_{sym}$(N—O) (FIG. 26D). The capability of functionalized graphene to form Meisenheimer complex provides a new method to control electronic structure and conjugate to biologically relevant species.

To conclude, this Example has described a method for spontaneous exfoliation of highly functionalized graphene directly from Hyper-3-Stage-1 GIC by reaction with an aryl diazonium salt solution under electrochemical reducing conditions. The successful covalent functionalization of the sp² carbon network of graphene with one group per 12 graphene C was obtained by first weakening the van der Waals attractions between graphene sheets by cation-π interacted GICs. This process comprised a reduction of the organization (crystallinity) of the intercalated ions, which was accomplished by partial reductive decomposition of the TBA⁺ cations. Highly expanded graphenes, characterized as Hyper-3-Stage-1 GIC ($d_{001}$-spacing >15.3 Å) were produced without any evidence of the creation of new covalent defects that disrupt the sp² lattice. The different intermediate Hyper-Stage-1 GICs were characterized by XRD, Raman spectroscopy, TEM and XPS. Raman analysis further confirmed the conversion of delocalized graphene sp² states to localized sp³ bonds with the functionalization with 3,5-DiNP groups. The formation of a Meisenheimer complex between 3,5-dinitrobenzene functionalized graphene with amines may have utility for creating new forms of functional graphenes.

Experimental Section

Electrochemical intercalation of graphite: HOPG intercalation was carried out in anhydrous DMF (2 mL) and MeCN (2 mL, dried over 3 Å molecular sieves) containing 1.5 M TBAP under N2 atmosphere. HOPG was connected to both negative and positive terminals of a potentiostat via alligator clips. The reference electrode was non-aqueous Ag/Ag⁺. (Note: at high negative voltage (~−1.3 V), electrolysis of water may disrupt the electrical contact of graphite domains and prevents effective intercalation, dry solvents may be desirable for effective in-situ intercalation). Linear voltage ramping conditions: −2.2 to −2.7 V at −40 µV s⁻¹ for Stage-1 GIC, −2.2 to −2.8 V at −40 µV s⁻¹ for Hyper-1-Stage-1 GIC, −2.8 to −2.9 V at −2 µV s⁻¹ for Hyper-2-Stage-1 GIC and −3.05 to −3.15 V at −3 µV s⁻¹ for Hyper-3-Stage-1 GIC. Applying a negative bias voltage resulted in intercalations of TBA⁺ cations, starting at the edges of graphite. When a voltage was applied, the morphology of graphite edges changed drastically within a few seconds. The edge of the graphite continued to expand and the increase in the thickness of the graphite layers could be observed visually.

Synthesis of 3,5-dinitrobenzenediazonium tetrafluoroborate: 3,5-dinitroaniline (1.83 g, 10.0 mmol) was dissolved in a mixture of tetrafluoroboric acid (48 wt %, 3.4 mL) and Milli-Q $H_2O$ (1.5 mL). The mixture was cooled to 0° C. A solution of sodium nitrite (690 mg, 10.0 mmol) in Milli-Q $H_2O$ (4.0 mL) was added slowly from behind a shield. (Note: diazonium salts are potentially explosive, and so a blast shield was used throughout the reaction.) The reaction was stirred vigorously for 30 min at 0° C. and filtered through a Büchner funnel. The solid was dissolved in minimum amount of acetone and the product was precipitated by addition of cold $Et_2O$. Pure 3,5-dinitrobenzenediazonium tetrafluoroborate (2.09 g, 74%) was collected by filtration through a Büchner funnel. ¹H NMR (400 MHz, Acetonitrile-d₃) δ 9.58 (d, J=2.0 Hz, 2H), 9.50 (t, J=2.0 Hz, 1H). ¹⁹F NMR (376 MHz, Acetonitrile-d₃) δ−151.10, −151.16. ¹³C NMR (126 MHz, Acetonitrile-d₃) δ 150.10, 133.53, 131.60, 119.66. ESI-HRMS: calculated for $C_6H_3N_4O_3^+$[M]⁺: 195.0149, found: 195.0158.

Electrochemical functionalization of graphene with 3,5-dinitrobenzenediazonium salt: In-situ functionalization was carried out by immersing Hyper-3-Stage-1 GIC in MeCN (4 mL) containing 0.1 M 3,5-dinitrobenzenediazonium tetrafluoroborate and 1 M TBAP under $N_2$ atmosphere. The voltage was linearly increased from −1.2 V to −2.2 V (vs. Ag/AgNO₃). During electrochemical grafting, nitrogen bubbles evolving from Hyper-3-Stage-1 GIC were observed. The functionalized graphene was then dispersed in MeCN by ultrasonication for a short time (e.g., 10 secs). Extensive washing steps were carried out to remove unreacted reagents and byproducts. Functionalized graphene was collected through a PTFE filter membrane with 0.1 µm pore size by vacuum filtration. A dispersion was used for characterization. The supernatant/centrifuged functionalized graphene dispersion was not used. The resultant functionalized graphenes were isolated from acetonitrile solutions and the purified materials were obtained by simple filtration followed by washing with solvents. The more ordered Hyper-1-Stage-1 GIC and Hyper-2-Stage-1 GIC had entirely crystalline $TBA^+$ intercalation layers and did not undergo spontaneous exfoliation in spite of the large graphene intersheet spacing when exposed to solutions containing reactive diazonium ions.

Mechanical exfoliation and analysis at the various levels of electrochemical activation, in the absence of diazonium ions, generated pristine defect free unfunctionalized graphenes. Samples were prepared by simple spin- or dropcasting of the functionalized graphene dispersion in MeCN onto substrates for Raman, IR, AFM, XPS and TEM. An exfoliated unfunctionalized graphene dispersion was prepared by ultrasonicating Hyper-3-Stage-1 in DMF overnight. The dispersion was filtered through a 0.1 µm pore Teflon membrane.

HOPG Electrochemical Intercalation

As shown in FIG. 9, scanning from −2.2 to −3.1 V resulted in cathodic peak currents believed to be associated with the intercalation of $TBA^+$ into the graphene galleries. The low intensity and broad breadth of (00ℓ) reflections suggest a lower degree of ordering along the c axis compared with those of highly oriented pyrolytic graphite (HOPG). The graphite staging phenomenon may be related to the periodic sequence of graphene gallery and intercalant layers, which may be distinct from disintegration of graphite domains. In graphite intercalation compounds (GICs), atomic or molecular layers of the intercalant may be inserted between the layers of graphite host material. GICs may be classified in stages 1, 2, . . . , n, where stage n means that one intercalant layer follows after n graphene layers. The stage index n may be given by the relation $L_c=(n-1)C_o+d_s$ where $C_o$ is the distance between adjacent graphite layers ($C_o$=3.35 Å) and $d_s$ is the distance between two graphene layers with an intercalant layer in between. The crystallographic evidence indicated that tetrabutylammonium ($TBA^+$) cations intercalated between each graphene layer. It is believed that the applied negative potential resulted in diffusion of $TBA^+$ cations into the graphene galleries, forming $TBA^+$-GIC. When the initial potential was above around −2.80 V (Ag/Ag$^+$), a Hyper-2-Stage-1 GIC was fully obtainable. As-prepared Stage-1 GIC was not observed to be capable of being fully converted to Hyper-2-Stage-1 GIC even the final voltage was applied above −3.15 V. Depending on the potentials, the $d_{001}$ spacing of GIC evolved from 8.17 to 12.7 to 15.3 Å, as shown in FIG. 12. It is believed that Hyper-1-Stage-1 and Hyper-2-Stage-1 contained more intercalated $TBA^+$ than Stage-1 GIC, and that these two compounds maintained every graphene sheet separated. It is believed that Hyper-1-Stage-1 and Hyper-2-Stage-1 were not Stage-n (n=2, 3 and 4) for n greater than 1. In addition, graphene grain boundaries (nanoscale width) on a HOPG were not visible using optical microscope. It is possible to determine whether the intercalation process occurs or not through colors/contrasts of GICs using the optical image as shown in FIG. 12. After $TBA^+$-intercalation, the domain boundaries of GICs were clearly distinguishable on the basis of contrast levels. It is interesting to note the surface contrast of GIC was similar to that of the few layer graphenes, indicating a single/few layer graphene sheets were separated or isolated. Hyper-3-Stage-1 GIC was achieved through a voltage ramp from −3.05 V to −3.15 V (vs. Ag/Ag$^+$) with an associated physical d-spacing expansion of graphite. The expected values (8.15 Å, 12.95 Å, and 15.35 Å, respectively) of $d_{001}$-spaacing of Stage-1, Hyper-1-Stage-1 and Hyper-2-Stage-1 with the height of flattened $TBA^+$ layer (~4.8 Å) and graphene (3.35 Å) matched with x-ray diffraction (XRD) data. The initial applied potential played a role in the generation of each Hyperstage-1 GIC. It is believed that full Hyper-1-Stage-1 GIC was not obtained because the reduction potentials for Hyper-1-Stage-1 and Hyper-2-Stage-1 GICs overlapped.

Proposed Reduction Mechanism of $TBA^+$

A proposed mechanism is that $TBA^+$ in the graphene galleries can be decomposed into tributylamine (n-Bu$_3$N), butene and alkanes which can then be trapped in the graphene galleries in FIG. 14A. The volume of Hyper-3-Stage-1 GIC in the graphene galleries expanded in vacuum (see FIG. 14B), which may indicate that gases are trapped in the graphene galleries. The $TBA^+$ may have acted as a frame to make electical contacts between graphene galleries. The disordered graphene galleries may have provided the space where electrochemial electron transfer occured between the basal plane of graphene and diazonium salt.

To confirm the electrochemical decomposition of $TBA^+$ to n-Bu$_3$N inside the graphene galleries, several NMR measurements were conducted (FIG. 15). After graphene intercalation was completed, an aliquot of the graphene electrolyte solution was removed and the $^1$H NMR was measured (FIG. 15). No trace of n-Bu$_3$N was observed in this case. This may indicate that $TBA^+$ decomposition did not occur on the surface of GIC and that the decomposed $TBA^+$ inside the GIC did not diffuse into the intercalation electrolyte solution. In another experiment, the GIC was transferred to a fresh solution of MeCN (~2 mL) and ultrasonication was applied to the mixture in order to exfoliate the GIC and release the intercalated ions and molecules into solution. The $^1$H NMR of the resulting GIC dispersion in MeCN was measured and tributylamine —NCH$_2$— and —CH$_3$ protons were observed. This data may show that $TBA^+$ indeed underwent partial electrochemical decomposition and that the decomposed product, tributylamine, was trapped inside the graphene galleries. The six —CH$_2$— protons of tributylamine overlapped with the —CH$_2$— protons of TBAP, therefore they cannot be distinguished. The $^1$H NMR of tributylamine and TBAP (FIG. 15) were overlaid with the above-mentioned spectra for peak identification and comparison.

Electrochemical Functionalization of Hyper-3-Stage-1 GIC

The functionalization on the basal planes of graphenes in Hyper-3-Stage-1 GIC occurred at higher electrochemical reduction potentials than those for the functionalization of the graphite surface. This high negative voltage (from −1.2 V) induced migration of solvated $TBA^+$/diazonium ions into the graphene interlayers (FIG. 16). The delocalized π-electrons of the basal plane of graphene underwent electron transfer reactions with the aryl diazonium cation, which became an aryl radical after dissociation and production of $N_2$. Diazonium cations/radicals surrounded by high density of $TBA^+$ effectively migrated into graphene interlayer. The aryl radical, which is believed to be highly reactive, readily formed a covalent bond with a carbon atom in the graphene lattice, changing its hybridization to that of an sp$^3$ C—C bond. It is believed that the high density of functional groups increased graphene solubility in MeCN and that the electrostatic repulsion force between adjacent graphenes assisted the exfoliation of functionalized graphene.

Spectroscopic Analysis

The basis of the shifts of the G band were observed in the Stage-1 and Hyperstage-1 GICs, indicating all the graphene layers in Stage-1 GICs were individually separated with the nearest graphene. In other words, each graphene layer was separated from its nearest neighbors. Raman 2D bands of Stage-1 and Hyperstage-1 GICs were not able to provide information on individual graphene separation (FIGS. 26A and 26B).

The functionalization induced amorphization/annihilation of the 2D band of graphene (which was no longer used to determine the number of layers). XPS spectra (FIG. 18C) showed large carbon-to-oxygen ratios for Hyperstage-1 GIC (C/O ~20); and exfoliated graphene (C/O ~39) showed a lower carbon-to-oxygen ratio, indicating a lower degree of oxidation, closer to that of the pristine graphite (C/O ~54)). N is peaks were observed after extensive washing and filtration of the functionalized graphene with organic solvents and drying the functionalized graphene samples in vacuum. No nitrogen was found in the unfunctionalized exfoliated graphene, suggesting that the nitrogen content on the graphene was originated from 3,5-dinitrobenzenediazonium functionalization. The G-band of exfoliated graphene showed a reversible behavior, its frequency and shape returned to that observed for HOPG, after the decoupling of $TBA^+$ cations from graphene.

The G-band of an initial staging GIC with $TBA^+$ split into two Raman peaks. It is believed that the peak at lower wave number (G) resulted from a vibrational mode of the inner graphene layers adjacent to other graphene layers, while the peak at higher wave number ($G_C$) was due to a vibrational mode of the boundary graphene layers adjacent to intercalant layers. The Raman $I_D/I_{D'}$ band intensity ratios of HOPG and exfoliated graphene were 0.67 and 2.4, respectively. It is believed that the D-band of exfoliated graphene was caused mainly by edge defects.

XRD of Exfoliated Graphene

Dropcasted exfoliated graphene on a substrate displayed a weakly reconstructed diffraction peak at $2\theta=26.27°$, which is the characteristic (002) reflection of graphite which originated from the interlayer distance between sheets.

XPS of Hyper-2-Stage1 and Hyper-3-Stage-1 GICs in Diazonium Functionalization

Upon application of a higher negative voltage ($-3.05$ V vs. $Ag/Ag^+$), the intercalated $TBA^+$ within the graphite sheets decomposed electrochemically (FIG. 22A). The N 1s XPS spectrum clearly shows the reduced form of $TBA^+$ in Hyper-3-stage-1 GICs (FIG. 22B). The area ratio among $NO_2$, NHOH and $NH_2$ on functionalized graphenes with 3,5-DiNP groups also showed this dependence on the applied voltages (FIG. 22B).

ATR-FTIR of 3,5-DiNP Functionalized Graphene

The peaks located at 1538.9 and 1344.4 $cm^{-1}$ were attributed to $\upsilon_{asym}$(N—O) and $\upsilon_{sym}$(N—O) bands, respectively.

AFM of 3,5-DiNP Functionalized Graphene

It was found that the domain size analysis was dependent on the sample preparation. TEM analysis of the dropcast functionalized graphene revealed an average area of ~3.14 $\mu m^2$ (FIG. 25). The smaller sizes observed in the AFM are believed to likely be the result of larger graphenes being removed by centrifugal force experienced with spincoating. The sizes of functionalized graphenes (without centrifugation and decantation) analyzed by TEM and AFM analysis ranged in size from 0.003 to 7.8 $\mu m^2$ and correlated well to the domain size distribution of the starting graphite.

UV-Vis and ATR-FTIR Analysis of Meisenheimer Complex

As a control experiment, the absorbance peak of 3,5-dinitrobenzenediazonium with n-butylamine shifted from 224 to 236 nm in FIG. 27A. The peaks for nitro groups on 3,5-dinitrobenzenediazonium located at 1552.9 and 1351.7 $cm^{-1}$ shifted to 1541.1 and 1347.9 $cm^{-1}$, respectively in FIG. 27B.

EXAMPLE 2

Figure 28:
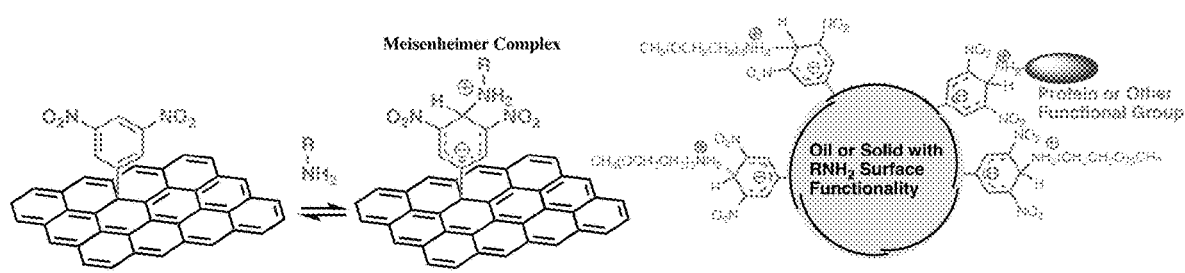
FIG. 28 shows a schematic depiction of a functionalized carbon-based material acting as a surfactant, in accordance with some embodiments.

This Example further describes a method for the reactive exfoliation of electrochemically activated graphite which gives stable solutions of functionalized graphene. This method was demonstrated using 3,5-dinitrophenydiazonium groups, which can produce surfaces capable dynamic covalent reactions with amines via Meisenheimer complexes (FIG. 28). It is believed that 1,3,5-trinitrobenzene binds 1-butyl amine with a $K_a=4.5\times10^4$ $M^{-1}$. It has been observed that the dinitrophenyl functionalized graphene displays Meisenheimer complexes with 1-butyl amine, and a weakening of the $NO_2$ infrared bands with a $-7.9$ $cm^-$shift in the $\upsilon_{asym}$(N—O) and a $-1.5$ $cm^{-1}$ shift in the $\upsilon_{sym}$(N—O) can be observed. This Example contemplates the creation and study dinitrophenyl:CNTs prepared using a diaryl iodonium functionalization scheme and/or a diazonium addition method. The sensory responses of the dinitrophenyl functionalized graphenes and SWCNTs to amines, in both in solution and vapor phase, may be evaluated. Considering the abundance of pendant amines in proteins, it is likely possible to perform multivalent bioconjugation reactions. Initial investigations may focus on confirming that conjugation occurs and to determine if bimolecular function is conserved. This can be evaluated with the used of fluorescently labeled antibodies or ligands to recognize bound proteins. The prospects for the immobilization of redox active enzymes may also be attractive. For these applications functionalized multi-walled and/or double-walled CNTs may be desirable if aryl functionalization disrupts the electrical transport of the SWCNTS and graphene. One example of an attractive enzyme is laccase, which, when combined with redox mediators, catalyzes a 4-electron reduction of $O_2$ to $H_2O$ at very low overpotentials at pH 5. Here, functional CNTs or graphenes may serve as the redox mediator.

Meisenheimer-graphenes can be used to modify/stabilize droplets or solids/nanoparticles. In the case of liquid droplets, 1,3-dinitrophenyl functionalized graphenes may be useful as surfactants (FIG. 28). The graphenes may be dispersed in water by forming Meisenheimer complexes with triethylene oxide amines and then exposed to liquid (oil) colloids stabilized with a $NH_2(CH_2)_3NH(CH_2)_{11}CH_3$ surfactant. Without wishing to be bound by any particular theory, it is predicted that interfacial amine exchange reactions will localize the graphene to the droplet surface. These approaches have the potential to create robust shells around the droplets, and as schematically illustrated in FIG. 28, multifunctional structures with the integration of proteins may be formed. Here, applications may include drug delivery. It may also be possible to coat solid particles and surfaces using Meisenheimer-graphenes. These graphenes can further potentially generate barrier layers, biocompatible surfaces, and/or corrosion/fouling resistant metal surfaces. Fouling of electrode surfaces is a problem in many electrochemical sensing schemes, and hence it may be advantageous to coat gold, platinum, nickel, and/or other low work function metals (e.g., Ti) with Meisenheimer-graphene. The coated electrode surfaces may have beneficial electrochemical performance in combination with aqueous redox species, such as $(Ru(NH_3)_6)^{2+/3+}$ and/or $Fe(CN)_6^{-3/-4}$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A carbon-based material, comprising:
   a carbon-based portion; and
   a functional group bonded to the carbon-based portion, wherein:
      the functional group is associated with a species via a reversible covalent bond, and
      carbon makes up greater than or equal to 30 wt % of the carbon-based portion.

2. The carbon-based material of claim 1, wherein the carbon-based portion comprises a two-dimensional material.

3. The carbon-based material of claim 1, wherein the carbon-based portion comprises elemental carbon.

4. The carbon-based material of claim 1, wherein the carbon-based portion comprises graphite.

5. The carbon-based material of claim 1, wherein the carbon-based portion comprises graphene.

6. The carbon-based material of claim 1, wherein the reversible covalent bond forms a portion of a Meisenheimer complex.

7. The carbon-based material of claim 1, wherein the functional group comprises a sulfonyl group.

8. The carbon-based material of claim 1, wherein the functional group comprises a ketone and/or aldehyde.

9. The carbon-based material of claim 1, wherein the functional group comprises a boronic acid group.

10. The carbon-based material of claim 1, wherein the functional group comprises a diene group.

11. The carbon-based material of claim 1, wherein the functional group comprises a dienophile group.

12. The carbon-based material of claim 1, wherein the species comprises an amine group.

13. The carbon-based material of claim 1, wherein the species comprises a diol group.

14. The carbon-based material of claim 1, wherein the species comprises a dienophile group.

15. The carbon-based material of claim 1, wherein the carbon-based portion comprises a plurality of carbon atoms and the carbon-based material comprises a plurality of functional groups bonded to the carbon-based portion, wherein a ratio of a total number of functional groups in the plurality of functional groups to a total number of carbon atoms in the plurality of carbon atoms is greater than or equal to 1:50.

16. The carbon-based material of claim 15, wherein the ratio of the total number of functional groups in the plurality of functional groups to the total number of carbon atoms in the plurality of carbon atoms is greater than or equal to 1:20.

17. The carbon-based material of claim 15, wherein the ratio of the total number of functional groups in the plurality of functional groups to the total number of carbon atoms in the plurality of carbon atoms is greater than or equal to 1:15.

18. The carbon-based material of claim 15, wherein the ratio of the total number of functional groups in the plurality of functional groups to the total number of carbon atoms in the plurality of carbon atoms is greater than or equal to 1:12.

19. The carbon-based material of claim 1, wherein the carbon-based portion comprises a plurality of graphene sheets, wherein greater than or equal to 70% of the graphene sheets are spaced apart from their nearest neighbors by a distance of greater than or equal to 10 Å.

20. The carbon-based material of claim 19, wherein the graphene sheets are uniformly spaced.

21. The carbon-based material of claim 19, wherein the graphene sheets are not uniformly spaced.

22. The carbon-based material of claim 19, wherein the carbon-based material comprises an ionic composition intercalated between the graphene sheets.

* * * * *